United States Patent [19]
Bouffard

Patent Number: 5,854,213
Date of Patent: Dec. 29, 1998

[54] ANTIFUNGAL CYCLOHEXAPEPTIDES

[75] Inventor: Frances A. Bouffard, Scotch Plains, N.J.

[73] Assignee: Merck & Co., Inc., Rahway, N.J.

[21] Appl. No.: 870,744

[22] Filed: Jun. 6, 1997

Related U.S. Application Data

[63] Continuation of Ser. No. 378,687, Jan. 26, 1995, abandoned.
[51] Int. Cl.$^6$ ............................ A61K 38/12; C07K 67/64
[52] U.S. Cl. ............................................. 514/11; 530/317
[58] Field of Search ............................... 514/11; 530/317

[56] References Cited

U.S. PATENT DOCUMENTS

| | | |
|---|---|---|
| 5,166,135 | 11/1992 | Schwatz . |
| 5,194,377 | 3/1993 | Schwartz et al. . |
| 5,202,309 | 4/1993 | Schwartz et al. . |
| 5,378,804 | 1/1995 | Balkovec et al. . |
| 5,516,756 | 5/1996 | Balkovec et al. . |
| 5,516,757 | 5/1996 | Balkovec et al. . |

FOREIGN PATENT DOCUMENTS

| | | |
|---|---|---|
| 851 310 | 8/1977 | Belgium . |
| 0 431 350 | 6/1991 | European Pat. Off. . |
| 0 462 531 | 12/1991 | European Pat. Off. . |
| 0 486 011 | 5/1992 | European Pat. Off. . |
| 0 535 967 A2 | 4/1993 | European Pat. Off. . |
| 0 561 639 A1 | 9/1993 | European Pat. Off. . |
| 2 365 554 | 4/1978 | France . |
| WO 94/25048 | 11/1994 | WIPO . |

OTHER PUBLICATIONS

Walzer, "Pneumocystis Carinii—New Clinical Spectrum . . ." *NEJM;* 324, No. 4, pp. 263–265, (Jan. 24, 1991).
Bartlett et al., "Pneumocystic Carinii, An Opportunists . . ." *Clinical Microbiology Reviews;* 4, No. 2, pp. 137–149, (Apr. 1991).
Schwartz et al., *J. Antibiotics;* 45 No. 12, pp. 1853–1866 (1992).
Walzer, et al., *Diagn. Microbiol. Infect. Dis;* 21, pp. 1–6 (1984).

*Primary Examiner*—Cecilia J. Tsang
*Assistant Examiner*—Patrick R. Delaney
*Attorney, Agent, or Firm*—Elliott Korsen; Mark R. Daniel

[57] ABSTRACT

The present invention is directed to novel carba cyclohexapeptide compounds of the formula

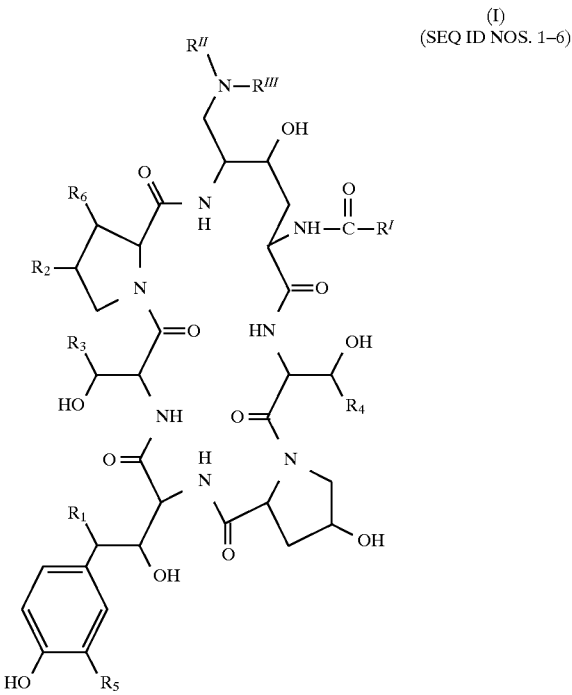

(I)
(SEQ ID NOS. 1–6)

where all substituents are defined herein, which are useful as antifungal agents and for the treatment of *Pneumocystis carinii* infections. Compositions containing the compounds of the invention are also disclosed.

17 Claims, No Drawings

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Xaa  Thr  Xaa  Xaa  Ser  Xaa
    1                        5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:2:

Xaa  Thr  Xaa  Xaa  Thr  Xaa
    1                        5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:3:

Xaa  Thr  Xaa  Xaa  Xaa  Xaa
    1                        5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:4:

Xaa  Ser  Xaa  Xaa  Ser  Xaa
    1                        5

( 2 ) INFORMATION FOR SEQ ID NO:5:

( i ) SEQUENCE CHARACTERISTICS:
        ( A ) LENGTH: 6 amino acids (B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:5:

```
Xaa Ser Xaa Xaa Thr Xaa
 1               5
```

(2) INFORMATION FOR SEQ ID NO:6:

(i) SEQUENCE CHARACTERISTICS:
(A) LENGTH: 6 amino acids
(B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:6:

```
Xaa Ser Xaa Xaa Xaa Xaa
 1               5
```

(2) INFORMATION FOR SEQ ID NO:7:

(i) SEQUENCE CHARACTERISTICS:
(A) LENGTH: 6 amino acids
(B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:7:

```
Xaa Thr Xaa Xaa Ser Xaa
 1               5
```

(2) INFORMATION FOR SEQ ID NO:8:

(i) SEQUENCE CHARACTERISTICS:
(A) LENGTH: 6 amino acids
(B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:8:

```
Xaa Thr Xaa Xaa Thr Xaa
 1               5
```

(2) INFORMATION FOR SEQ ID NO:9:

(i) SEQUENCE CHARACTERISTICS:
(A) LENGTH: 6 amino acids
(B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:9:

```
Xaa Thr Xaa Xaa Xaa Xaa
 1               5
```

(2) INFORMATION FOR SEQ ID NO:10:

(i) SEQUENCE CHARACTERISTICS:
(A) LENGTH: 6 amino acids (B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:10:

Xaa  Ser  Xaa  Xaa  Ser  Xaa
 1                     5

(2) INFORMATION FOR SEQ ID NO:11:

(i) SEQUENCE CHARACTERISTICS:
    (A) LENGTH: 6 amino acids
    (B) TYPE: amino acid
    (C) STRANDEDNESS: unknown
    (D) TOPOLOGY: circular (ii) MOLECULE TYPE: peptide (xi) SEQUENCE DESCRIPTION: SEQ ID NO:11:

Xaa  Ser  Xaa  Xaa  Thr  Xaa
 1                     5

(2) INFORMATION FOR SEQ ID NO:12:

(i) SEQUENCE CHARACTERISTICS:
    (A) LENGTH: 6 amino acids
    (B) TYPE: amino acid
    (C) STRANDEDNESS: unknown
    (D) TOPOLOGY: circular (ii) MOLECULE TYPE: peptide (xi) SEQUENCE DESCRIPTION: SEQ ID NO:12:

Xaa  Ser  Xaa  Xaa  Xaa  Xaa
 1                     5

(2) INFORMATION FOR SEQ ID NO:13:

(i) SEQUENCE CHARACTERISTICS:
    (A) LENGTH: 6 amino acids
    (B) TYPE: amino acid
    (C) STRANDEDNESS: unknown
    (D) TOPOLOGY: circular (ii) MOLECULE TYPE: peptide (xi) SEQUENCE DESCRIPTION: SEQ ID NO:13:

Xaa  Thr  Xaa  Xaa  Ser  Xaa
 1                     5

(2) INFORMATION FOR SEQ ID NO:14:

(i) SEQUENCE CHARACTERISTICS:
    (A) LENGTH: 6 amino acids
    (B) TYPE: amino acid
    (C) STRANDEDNESS: unknown
    (D) TOPOLOGY: circular (ii) MOLECULE TYPE: peptide (xi) SEQUENCE DESCRIPTION: SEQ ID NO:14:

Xaa  Thr  Xaa  Xaa  Thr  Xaa
 1                     5

(2) INFORMATION FOR SEQ ID NO:15:

(i) SEQUENCE CHARACTERISTICS:
    (A) LENGTH: 6 amino acids (B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:15:

```
Xaa  Thr  Xaa  Xaa  Xaa  Xaa
 1                 5
```

(2) INFORMATION FOR SEQ ID NO:16:

(i) SEQUENCE CHARACTERISTICS:
    (A) LENGTH: 6 amino acids
    (B) TYPE: amino acid
    (C) STRANDEDNESS: unknown
    (D) TOPOLOGY: circular (ii) MOLECULE TYPE: peptide (xi) SEQUENCE DESCRIPTION: SEQ ID NO:16:

```
Xaa  Ser  Xaa  Xaa  Ser  Xaa
 1                 5
```

(2) INFORMATION FOR SEQ ID NO:17:

(i) SEQUENCE CHARACTERISTICS:
    (A) LENGTH: 6 amino acids
    (B) TYPE: amino acid
    (C) STRANDEDNESS: unknown
    (D) TOPOLOGY: circular (ii) MOLECULE TYPE: peptide (xi) SEQUENCE DESCRIPTION: SEQ ID NO:17:

```
Xaa  Ser  Xaa  Xaa  Thr  Xaa
 1                 5
```

(2) INFORMATION FOR SEQ ID NO:18:

(i) SEQUENCE CHARACTERISTICS:
    (A) LENGTH: 6 amino acids
    (B) TYPE: amino acid
    (C) STRANDEDNESS: unknown
    (D) TOPOLOGY: circular (ii) MOLECULE TYPE: peptide (xi) SEQUENCE DESCRIPTION: SEQ ID NO:18:

```
Xaa  Ser  Xaa  Xaa  Xaa  Xaa
 1                 5
```

(2) INFORMATION FOR SEQ ID NO:19:

(i) SEQUENCE CHARACTERISTICS:
    (A) LENGTH: 6 amino acids
    (B) TYPE: amino acid
    (C) STRANDEDNESS: unknown
    (D) TOPOLOGY: circular (ii) MOLECULE TYPE: peptide (xi) SEQUENCE DESCRIPTION: SEQ ID NO:19:

```
Xaa  Thr  Xaa  Xaa  Ser  Xaa
 1                 5
```

(2) INFORMATION FOR SEQ ID NO:20:

(i) SEQUENCE CHARACTERISTICS:
    (A) LENGTH: 6 amino acids (B) TYPE: amino acid
(C) STRANDEDNESS: unknown
(D) TOPOLOGY: circular (i i) MOLECULE TYPE: peptide (x i) SEQUENCE DESCRIPTION: SEQ ID NO:20:

Xaa  Thr  Xaa  Xaa  Thr  Xaa
 1                 5

(2) INFORMATION FOR SEQ ID NO:21:

(i) SEQUENCE CHARACTERISTICS:
(A) LENGTH: 6 amino acids
(B) TYPE: amino acid
(C) STRANDEDNESS: unknown
(D) TOPOLOGY: circular (i i) MOLECULE TYPE: peptide (x i) SEQUENCE DESCRIPTION: SEQ ID NO:21:

Xaa  Thr  Xaa  Xaa  Xaa  Xaa
 1                 5

(2) INFORMATION FOR SEQ ID NO:22:

(i) SEQUENCE CHARACTERISTICS:
(A) LENGTH: 6 amino acids
(B) TYPE: amino acid
(C) STRANDEDNESS: unknown
(D) TOPOLOGY: circular (i i) MOLECULE TYPE: peptide (x i) SEQUENCE DESCRIPTION: SEQ ID NO:22:

Xaa  Ser  Xaa  Xaa  Ser  Xaa
 1                 5

(2) INFORMATION FOR SEQ ID NO:23:

(i) SEQUENCE CHARACTERISTICS:
(A) LENGTH: 6 amino acids
(B) TYPE: amino acid
(C) STRANDEDNESS: unknown
(D) TOPOLOGY: circular (i i) MOLECULE TYPE: peptide (x i) SEQUENCE DESCRIPTION: SEQ ID NO:23:

Xaa  Ser  Xaa  Xaa  Thr  Xaa
 1                 5

(2) INFORMATION FOR SEQ ID NO:24:

(i) SEQUENCE CHARACTERISTICS:
(A) LENGTH: 6 amino acids
(B) TYPE: amino acid
(C) STRANDEDNESS: unknown
(D) TOPOLOGY: circular (i i) MOLECULE TYPE: peptide (x i) SEQUENCE DESCRIPTION: SEQ ID NO:24:

Xaa  Ser  Xaa  Xaa  Xaa  Xaa
 1                 5

ANTIFUNGAL CYCLOHEXAPEPTIDES

This is a continuation of application Ser. No. 08/378,687 filed on Jan. 26, 1995 now abandoned.

BACKGROUND OF THE INVENTION

The present invention is directed to novel cyclohexapeptide compounds which are useful as antifungal and anti-Pneumocystis agents.

There presently exists a need for antifungal and anti-Pneumocystis agents due to an increase in the number of isolates which are resistant to conventional agents. Additionally, conventional agents show somewhat high levels of toxicity which limit their usefulness. Lastly, the incidence of *Pneumocystis carinii* pneumonia is increasing, particularly in view of the high incidence of immunocompromised patients susceptible to infection, such as those suffering from AIDS.

SUMMARY OF THE INVENTION

The compounds of the present invention, Compound I (Seq. ID Nos. 1–6), are characterized in having a carbon attached to the cyclohexapeptide ring at the 5-carbon of the 4-hydroxyornithine component (hereinafter "C-5-orn") and may be represented by the formula:

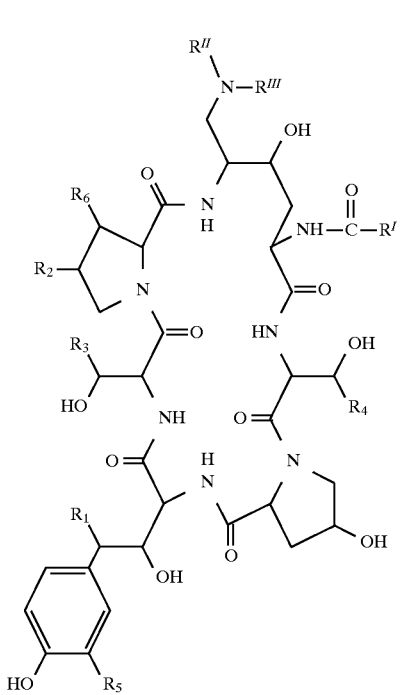

(I)
(SEQ ID NOS. 1–6)

wherein
$R_1$ is H or OH;
$R_2$ is H, $CH_3$ or OH;
$R_3$ is H, $CH_3$, $CH_2CONH_2$, $CH_2CN$, $CH_2CH_2NR^{II}R^{III}$, $CH_2CH_2N(R^{IV})_3{}^+X^-$ or $CH_2CH_2NH(C=NH)R^{VII}$;
$R_4$ is H or $CH_3$;
$R_5$ is H, OH or $OSO_3H$;
$R_6$ is H or OH;
$R^I$ is $C_9$–$C_{21}$ alkyl, $C_9$–$C_{21}$ alkenyl, $C_1$–$C_{10}$ alkoxyphenyl, $C_1$–$C_{10}$ alkoxynaphthyl, or

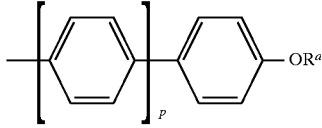

wherein
$R^a$ is $C_1$–$C_{10}$ alkyl; or $(CH_2)_qNR^bR^c$ wherein $R^b$ and $R^c$ are independently H, $C_1$–$C_{10}$ alkyl or $R^b$ and $R^c$ taken together with the nitrogen atom are

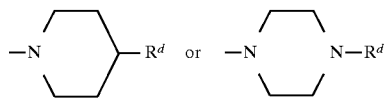

wherein
$R^d$ is $C_1$–$C_{16}$ alkyl, cyclohexylmethyl, phenyl or benzyl;
p is 1 or 2; and
q is 2, 3 or 4;
$R^{II}$ is H, $C_1$–$C_4$ alkyl, $(CH_2)_{2-4}OH$, $C=NH(R^{VII})$, $(CH_2)_{2-4}NR^VR^{VI}$, $(CH_2)_{2-4}N(R^{IV})_3{}^+X^-$, $(CH_2)_{2-4}NH(C=NH)R^{VII}$, $(CH_2)_{1-4}CH(NR^VR^{VI})(CH_2)_{1-4}NR^VR^{VI}$, $(CH_2)_{2-4}NR^V(CH_2)_{2-4}NR^VR^{VI}$, $CO(CH_2)_{1-4}NR^VR^{VI}$, $COCH(NR^VR^{VI})(CH_2)_{1-4}NR^VR^{VI}$;
$R^{III}$ is H, $C_1$–$C_4$ alkyl, $(CH_2)_{2-4}NR^VR^{VI}$, $(CH_2)_{2-4}N(R^{IV})_3{}^+X^-$, $(CH_2)_{2-4}NH(C=NH)R^{VII}$, $(CH_2)_{1-4}CH(NR^VR^{VI})(CH_2)_{1-4}NR^VR^{VI}$, $(CH_2)_{2-4}NR^V(CH_2)_{2-4}NR^VR^{VI}$; or
$R^{II}$ and $R^{III}$ taken together are $-(CH_2)_4-$, $-(CH_2)_5-$, $-(CH_2)_2O(CH_2)_2-$, or $-(CH_2)_2NH(CH_2)_2-$;
$R^{IV}$ is $C_1$–$C_4$ alkyl;
$R^V$ is H or $C_1$–$C_4$ alkyl;
$R^{VI}$ is H or $C_1$–$C_4$ alkyl;
$R^{VII}$ is H, $C_1$–$C_4$ alkyl or $NH_2$;
X is Cl, Br or I; or
a pharmaceutically acceptable salt thereof.

Additionally, there are disclosed quaternary ammonium salts of the formula

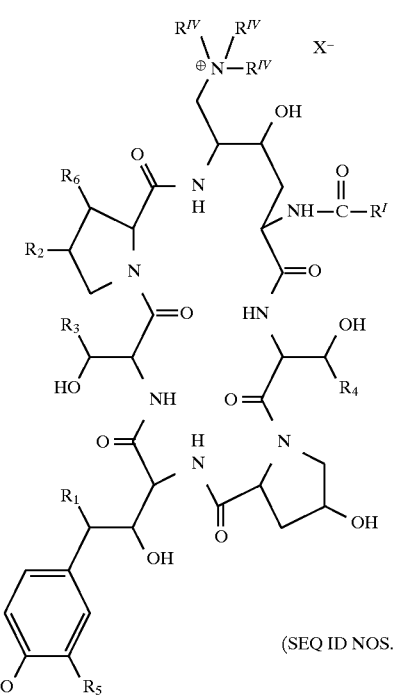

(SEQ ID NOS. 1-6)

where $R_1$, $R_2$, $R_3$, $R_4$, $R_5$, $R_6$, $R^I$, $R^{IV}$ and X are as previously defined.

There are also disclosed compounds of the formula

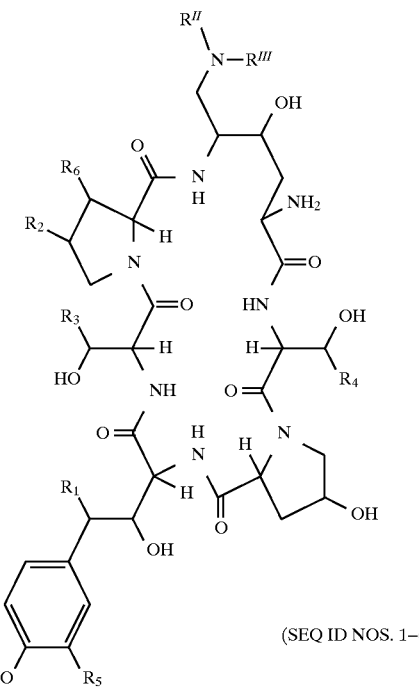

(SEQ ID NOS. 1-6)

wherein
$R_1$ is H or OH;
$R_2$ is H, $CH_3$ or OH;
$R_3$ is H, $CH_3$, $CH_2CONH_2$, $CH_2CN$, $CH_2CH_2NR^{II}R^{III}$, $CH_2CH_2N(R^{IV})_3{}^+X^-$ or $CH_2CH_2NH(C=NH)R^{VII}$;
$R_4$ is H or $CH_3$;
$R_5$ is H, OH or $OSO_3H$;
$R_6$ is H or OH;
$R^{II}$ is H, $C_1$–$C_4$ alkyl, $(CH_2)_{2-4}OH$, $C=NH(R^{VII})$, $(CH_2)_{2-4}NR^VR^{VI}$, $(CH_2)_{2-4}N(R^{IV})_3{}^+X^-$, $(CH_2)_{2-4}NH(C=NH)R^{VII}$, $(CH_2)_{1-4}CH(NR^VR^{VI})(CH_2)_{1-4}NR^VR^{VI}$, $(CH_2)_{2-4}NR^V(CH_2)_{2-4}NR^VR^{VI}$, $CO(CH_2)_{1-4}NR^VR^{VI}$, $COCH(NR^VR^{VI})(CH_2)_{1-4}NR^VR^{VI}$;
$R^{III}$ is H, $C_1$–$C_4$ alkyl, $(CH_2)_{2-4}NR^VR^{VI}$, $(CH^2)_{2-4}N(R^{IV})_3{}^+X^-$, $(CH^2)_{2-4}NH(C=NH)R^{VII}$, $(CH_2)_{1-4}CH(NR^VR^{VI})(CH_2)_{1-4}NR^VR^{VI}$, $(CH_2)_{2-4}NR^V(CH_2)_{2-4}NR^VR^{VI}$; or
$R^{II}$ and $R^{III}$ taken together are $-(CH_2)_4-$, $-(CH_2)_5-$, $-(CH_2)_2O(CH_2)_2-$, or $-(CH_2)_2NH(CH_2)_2-$;
$R^{IV}$ is $C_1$–$C_4$ alkyl;
$R^V$ is H or $C_1$–$C_4$ alkyl;
$R^{VI}$ is H or $C_1$–$C_4$ alkyl;
$R^{VII}$ is H, $C_1$–$C_4$ alkyl or $NH_2$;
X is Cl, Br or I; or a pharmaceutically acceptable salt thereof, which are useful for the preparation of Compounds I and II of the invention.

Preferred embodiments of the invention are those of Compound I wherein
$R_1$ and $R_6$ are OH
$R_2$ and $R_5$ are H
$R_3$ is $CH_2CH_2NH_2$
$R_4$ is $CH_3$
$R^I$ is 9,11-dimethyltridecyl,

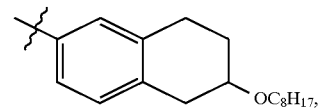

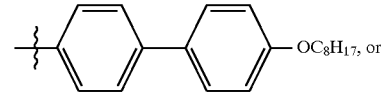

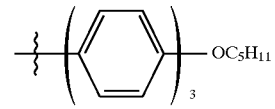

$R^{II}$ is H, $CH_2CH_2NH_2$, $COCH_2NH_2$, $COCH_2CH_2NH_2$ or $COCH(NH_2)CH_2NH_2$, and
$R^{III}$ is H.

The compounds of this invention may be formulated into pharmaceutical compositions which are comprised of the compounds of formula I or II in combination with a pharmaceutically acceptable carrier.

The compounds of this invention are useful in treating fungal infections such as those caused by Candida and Aspergillus and for the treatment and prevention of infections caused by *Pneumocystis carinii*. These infections are often found in immunocomprised patients such as those suffering with AIDS.

Throughout the specification and appended claims, a given chemical formula or name shall encompass all optical and stereoisomers as well as racemic mixtures where such isomers and mixtures exist.

The term alkyl refers to straight, branched or cyclic chain hydrocarbon groups, e.g., methyl, ethyl, n-propyl, isopropyl, n-butyl, pentyl, hexyl, heptyl, cyclopentyl, cyclohexyl, cyclohexylmethyl and the like.

The term cycloalkyl refers to a species of alkyl containing from 3 to 15 carbon atoms without alternating or resonating double bonds between carbon atoms.

The term alkenyl refers to groups such as, e.g., vinyl, 1-propene-2-yl, 1-butene-4-yl, 2-buten-4-yl, 1-pentene-5-yl and the like.

The term alkoxy refer to straight or branched chain oxyalkyl groups such as, e.g., methoxy, ethoxy, butoxy, heptoxy, dodecyloxy, and the like.

The compounds of the present invention are generally obtained as mixtures of stereoisomeric forms in which one form usually predominates. Conditions may be adjusted by means within the normal skill of the skilled artisan to obtain predominantly the desired isomer. The compounds with preferred stereoisomeric form designated herein as the "normal" form are those in which the group at the "C-5-orn" position is below the plane at the said position. The designation "epi" has been employed for those compounds in which the group at the "C-5-orn" position is above the plane.

Pharmaceutically acceptable salts suitable as acid addition salts are those from acids such as hydrochloric, hydrobromic, phosphoric, sulfuric, maleic, citric, acetic, tartaric, succinic, oxalic, malic, glutamic and the like, and include other acids related to the pharmaceutically acceptable salts listed in *Journal of Pharmaceutical Science*, 66:2 (1977).

When the acyl substituent at the 2-position on the 4-hydroxyornithine nitrogen contains an aromatic chain, it differs from natural products and known compounds. The aromatic chain disclosed contains one to three phenyl groups further extended by substituents in the para position.

Representative nuclei for the derivatives of the present invention (Compounds I & II) and the sequence ID for these compounds may be seen in the following table. Since the peptide nuclei would be the same irrespective of substituents $R_1$, $R_2$, $R_5$, $R_6$, $R^I$, $R^{II}$, or $R^{III}$ and since the sequence identification number is assigned for the nuclear variations, the amines and salts have the same sequence ID's.

| Carba Compound | $R_3$ | $R_4$ | SEQ ID NO. |
|---|---|---|---|
| I-1 | H | $CH_3$ | 1 |
| I-2 | $CH_3$ | $CH_3$ | 2 |
| I-3 | All Others | $CH_3$ | 3 |
| I-4 | H | H | 4 |
| I-5 | $CH_3$ | H | 5 |
| I-6 | All Others | H | 6 |

The compounds of the present invention are soluble in water, lower alcohols, and polar aprotic solvents such as N,N-dimethylformamide (DMF), dimethyl sulfoxide (DMSO) and pyridine. They are insoluble in solvents such as diethyl ether and acetonitrile.

The compounds of the present invention are useful as an antibiotic, especially as an antifungal agent or as an antiprotozoal agent. As antifungal agents they are useful for the control of both filamentous fungi and yeasts. They are especially adaptable to be employed for the treatment of mycotic infections in mammals, especially those caused by Candida species such as *C. albicans, C. tropicalis* and *C. pseudotropicalis,* Cryptococcus species such as *C. neoformans* and Aspergillus species such as *A. fumigatus, A. flavus* and *A. niger.* They are also useful for the treatment and/or prevention of *Pneumocystis carinii* pneumonia to which immune-compromised patients are especially susceptible as hereinafter described.

The structural aspect which distinguishes the compounds of the present invention from previously disclosed cyclohexapeptides is the carbon attached to the cyclohexapeptide ring at the 5-carbon of the 4-hydroxyornithine residue.

The most important naturally occurring echinocandins and pneumocandins have a labile C—O bond at the C-5 orn position. Other pneumocandins as disclosed in U.S. Pat. No. 5,378,804 issued Jan. 3, 1995 have a labile C—N bond at the C-5 orn. The compounds disclosed herein have a C—C bond at the C-5 orn imparting stability to the compounds while still retaining potent antifungal and anti-Pneumocystis activity.

The compounds of the present invention may be prepared from cyclohexapeptides having the formula

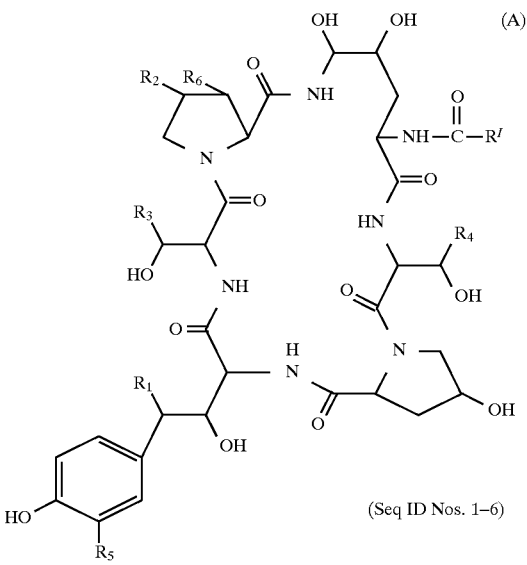

(Seq ID Nos. 1–6)

by a series of reactions in which the oxygen atom at the "C-5-orn" (which also may be referred to as the hemiaminal position) is ultimately replaced by carbon. The starting materials may be natural products or modified natural products as subsequently described.

The sequence IDs of the starting materials are listed in the following table:

| Compound | $R_3$ | $R_4$ | Starting Material SEQ ID NO. |
|---|---|---|---|
| A-1 | H | $CH_3$ | 7 |
| A-2 | $CH_3$ | $CH_3$ | 8 |
| A-3 | All Others | $CH_3$ | 9 |
| A-4 | H | H | 10 |
| A-5 | $CH_3$ | H | 11 |
| A-6 | All Others | H | 12 |

A compound where $R_1$ is OH, $R_2$ is H, $R_3$ is $CH_2CONH_2$, $R_4$ is $CH_3$, $R_5$ is H and $R_6$ is OH and $R^I$ is dimethyltridecyl has been identified in the literature as pneumocandin $B_o$; a similar compound where $R_2$ is $CH_3$, has been identified as pneumocandin $A_o$ and a third compound where $R_2$ is OH and $R_6$ is H has been identified as pneumocandin $C_o$ (*J. Antibiotics* 45:1855–60, December 1992). A similar compound where $R_2$ and $R_6$ are OH and $R^I$ is dimethyltridecyl has been identified as pneumocandin $D_o$ (*J. Antibiotics* 47:755–764, July 1994).

When in the starting compound, $R_3$ is H, $CH_3$ or $CH_2CONH_2$, they may be directly employed. When $R_3$ is $CH_2CN$, $CH_2CH_2NR^{II}R^{III}$, $CH_2CH_2N(R^{IV})_3{}^+X^-$ or $CH_2CH_2NH(C=NH)R^{VII}$, the amides must be first converted to $CH_2CN$ or $CH_2CH_2NH_2$ and then modified.

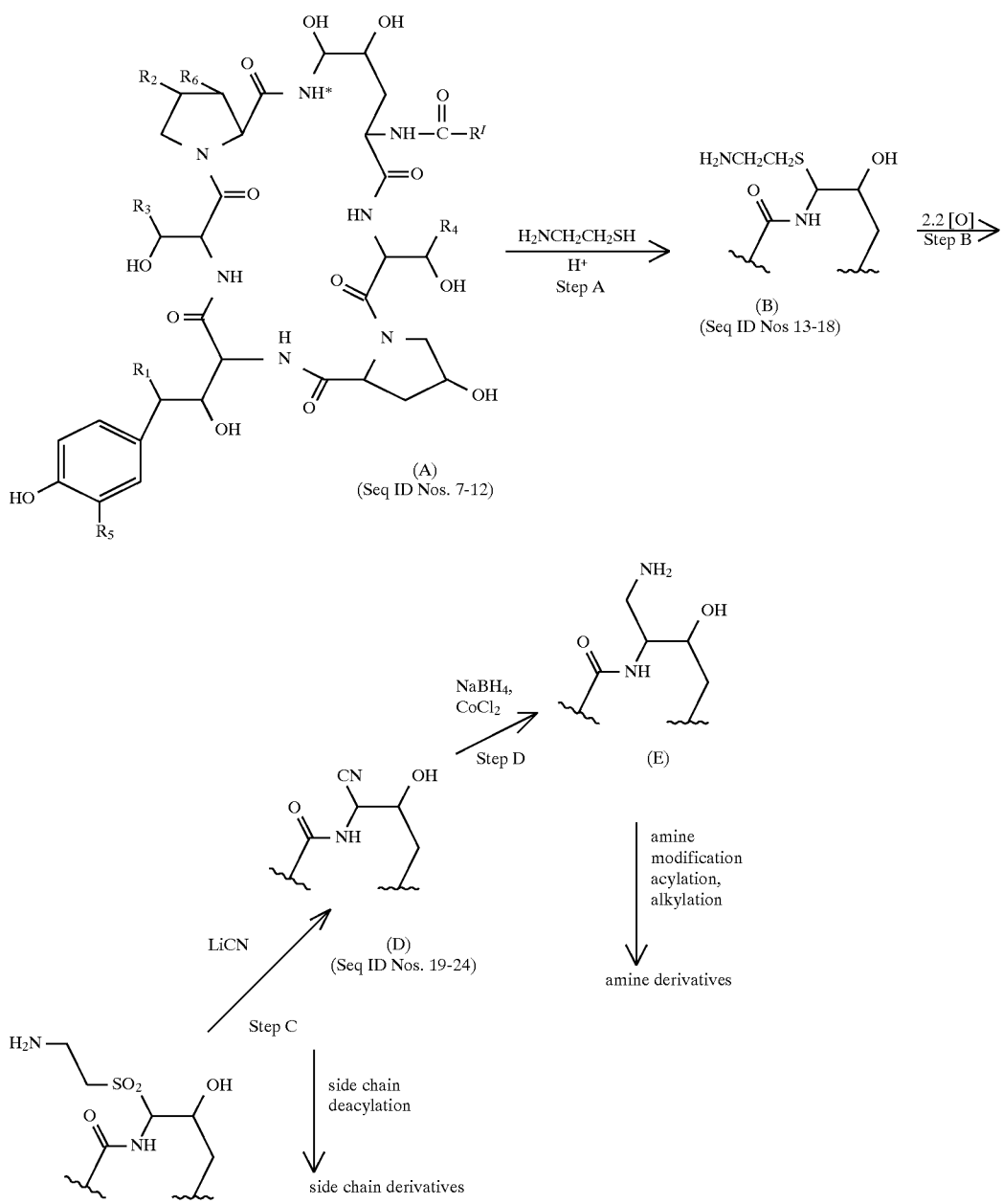

* The position is the "C-5-orn" or the hemiaminal position.

In Step A, the starting material, Compound A, an alkylthiol or arylthiol and acid are caused to react in an aprotic solvent under anhydrous conditions for time sufficient for reaction to take place with the formation of Compound B (Seq ID Nos. 13–18), listed in the following table. Aminoethanethiol has been found to be especially useful for this step.

| Compound | $R_3$ | $R_4$ | Sulfur Intermediate SEQ ID NO. |
|---|---|---|---|
| B-1 | H | $CH_3$ | 13 |
| B-2 | $CH_3$ | $CH_3$ | 14 |

-continued

| Compound | $R_3$ | $R_4$ | Sulfur Intermediate SEQ ID NO. |
|---|---|---|---|
| B-3 | All Others | $CH_3$ | 15 |
| B-4 | H | H | 16 |
| B-5 | $CH_3$ | H | 17 |
| B-6 | All Others | H | 18 |

For Step A, suitable acids include strong organic acid and mineral acids. Examples of strong organic acids are camphorsulfonic acid, p-toluenesulfonic acid, trifluoroacetic acid and methanesulfonic acid. Mineral acids include hydrochloric acid and hydrobromic acid. Camphorsulfonic acid is preferred.

Suitable solvents include DMF, DMSO, 1-methyl-2-pyrrolidinone and hexamethyl phosphoric triamide (HMPA). DMF or DMSO is preferred.

The reaction is generally carried out at ambient temperature to 60° C. for about 3 hours to about 10 days.

In carrying out the reaction, the cyclohexapeptide compound, the thiol compound and acid are stirred together in a suitable solvent until the reaction is substantially complete. The reaction mixture then is diluted with water and flash chromatographed on reverse phase resins using 10 to 40 percent acetonitrile/water (containing 0.1% trifluoroacetic acid) as eluant. Trifluoroacetic acid may hereinafter be designated "TFA". The fractions containing the desired product may be concentrated and lyophilized and the lyophilized material purified by preparative high performance liquid chromatography (HPLC).

Appropriate columns for HPLC are commercially available columns sold under trademarks or trade names such as "ZORBAX" (DuPont), "DeltaPak" (Waters), "LICHROPREP" RP18 (E. Merck). The specific columns are identified in the working examples.

In Step B, Compound C (Seq ID Nos. 13–18), a sulfone is obtained by the oxidation of Compound B. Suitable oxidizing agents or oxidants include "OXONE" ($KHSO_5 \cdot KHSO_4 \cdot K_2SO_4$ 2:1:1, Aldrich Chemicals), metachloroperoxybenzoic acid, and peroxyacetic acid. The sequence ID of Compound C is the same as that of Compound B since the atom attached to the hemiaminal carbon is still sulfur. Thus, the sequence IDs of the sulfones are as follows:

| Compound | $R_3$ | $R_4$ | Sulfone SEQ ID NO. |
| --- | --- | --- | --- |
| C-1 | H | $CH_3$ | 13 |
| C-2 | $CH_3$ | $CH_3$ | 14 |
| C-3 | All Others | $CH_3$ | 15 |
| C-4 | H | H | 16 |
| C-5 | $CH_3$ | H | 17 |
| C-6 | All Others | H | 18 |

The oxidation of the thioether (Compound B) to the sulfone (Compound C) is carried out with about two molar amounts of the oxidant. When one molar amount of oxidant is employed, the product is a sulfoxide which may then be converted to the sulfone. The sulfoxides may be employed as an intermediate in the formation of the nitrite but the sulfone is preferred. A slight excess over the two molar amount of the oxidizing agent is employed.

The reaction is carried out in an aqueous medium, preferably a mixture of acetonitrile and water. About equal amounts are preferred although a range of 1:9 to 9:1 may be employed.

In carrying out the reaction, the oxidant is added to a solution of Compound B (Seq ID Nos. 13–18) in 1:1 acetonitrile/water and the mixture allowed to stand at ambient temperature for time sufficient to complete the reaction to obtain Compound C generally from about 30 minutes to one hour.

After completion of the reaction, the compound is recovered from the reaction mixture by diluting with water and chromatographing. Reverse phase (C18) flash column chromatography is suitable in this purification step. The preferred eluting agent is 30–45 percent acetonitrile/water (0.1% TFA) in 5 percent step gradients. The appropriate fractions are lyophilized to recover the desired sulfone intermediate, Compound C (Seq ID Nos. 13–18). The intermediate tends to be labile, thus the isolation should be carried out as rapidly as possible. Alternatively, the reaction mixture can be lyophilized and the crude sulfone used as is in the subsequent step.

Compound C may be converted to a compound having a carbon directly attached to the "C-5-orn". As seen in the flow diagram, reaction of Compound C with an alkali metal cyanide produces a nitrile at that position (Compound D). The nitrile can subsequently be reacted with sodium borohydride and cobaltous chloride to afford the aminoalkyl substituent which may be converted into a substituted amine as subsequently described. Compound D is an important intermediate for most of the compounds of the present invention. Sequence ID Nos. for Compound D, the nitrile, are listed in the following table:

| Compound | $R_3$ | $R_4$ | Nitrile SEQ ID NO. |
| --- | --- | --- | --- |
| D-1 | H | $CH_3$ | 19 |
| D-2 | $CH_3$ | $CH_3$ | 20 |
| D-3 | All Others | $CH_3$ | 21 |
| D-4 | H | H | 22 |
| D-5 | $CH_3$ | H | 23 |
| D-6 | All Others | H | 24 |

The nitrile may be obtained by adding alkali metal cyanide while stirring at ambient temperature to a solution of the sulfone in an aprotic solvent for time sufficient to complete the reaction with the formation of the cyanide as determined by HPLC analysis. The reaction mixture then may be diluted with water and then chromatographed to separate the desired nitrile (Compound D) from the reaction mixture. Reverse-phase (C18) flash column chromatography using 20–60% acetonitrile/water (0.1% TFA) in 10% step gradients is suitable for this procedure.

The nitrile (Compound D) may then be reduced to a compound having a free amino group (Compound E).

The reduction may be carried out employing either chemical or catalytic reduction. When chemical reduction is employed, hydride or hydride combinations have been found useful.

Sodium borohydride with cobaltous chloride in alcoholic solvent has been found to be particularly useful. When this combination of reagents is used, from about 5 to 50 molar equivalents of sodium borohydride and from 2 to 20 molar equivalents of cobaltous chloride are used for each molar amount of the nitrile.

Other reducing agents such as Raney nickel, sodium cyanoborohydride, aluminum hydride, diborane, diisobutyl aluminum hydride and the like may also be used. Frequently these reducing agents are used in combination with a Lewis acid such as cobaltous chloride or aluminum chloride as in the present combination of sodium borohydride and cobaltous chloride.

Catalytic hydrogenation also may be carried out over a variety of catalysts including palladium on carbon, platinum oxide or rhodium on alumina. Low pressure catalytic reduction over Pd/C as the catalyst is especially preferred.

Typical solvents depending on the reagent include alcohols, especially methanol and ethanol; dimethylformamide, pyridine, tetrahydrofuran or other ethers.

Compounds containing a selectively derivatized amine at the C5-orn position in the presence of an amine at $R_3$ (i.e. $R_3=CH_2CH_2NH_2$) may be prepared by initially introducing the C5-orn amine when $R_3=CH_2CONH_2$. The C5-orn amine may then be substituted to provide compounds where $R^{II}$ and $R^{III}$ are not H. Finally, the primary amide at $R_3$ may be converted to an amine following established procedures. Alternatively, the amine of $R_3$ may be protected as a CBZ derivative prior to reduction of the C5-orn nitrile to an amine.

The amine thus obtained may be converted into an acylated amine by conventional means using a CBZ protected amino acid to obtain, after deprotection, Compound I where $R^{II}$ is $COCH(NH_2)(CH_2)_{1-4}NH_2$ and $R^{III}$ is H.

Compound I where $R^{II}$ and/or $R^{III}$ are alkyl may be prepared using any suitable known procedure for preparing secondary or tertiary amines. When the desired alkyl group on the nitrogen is methyl, the carbon may be introduced by formylating, followed by reduction of the hydroxymethyl group with sodium cyanoborohydride or other reducing agent. Alternatively, alkylation may be carried out by causing an appropriately substituted alkyl halide to react with the amine in an aprotic solvent in the presence of a base.

To prepare compounds in which the $R_3$ amine (i.e. $R_3 = CH_2CH_2NH_2$) is selectively derivatized in the presence of an amine at C5-orn, the $R_3$ amine may be substituted prior to reduction of the nitrile at C5-orn.

The invention also embraces quaternary ammonium salts of formula (II). These may be prepared by treatment of an amine with an alkyl halide and base in a protic or aprotic solvent. A typical procedure would be to add excess methyl iodide to a solution of the amine and sodium bicarbonate in DMF at room temperature. The product may be isolated by diluting with $H_2O$ followed by C18 HPLC.

The invention also embraces acid addition salts. The compound in the normal course of isolation is obtained as an acid addition salt. Generally, it is as a trifluoroacetic acid or acetic acid salt. The salt thus obtained may be dissolved in water and passed through an anion exchange column bearing the desired anion. The eluate containing the desired salt may be concentrated to recover the salt as a solid product.

The compounds of the present invention are water soluble in their protonated or permanently charged quaternary forms. This is an advantage over the neutral, uncharged echinocandins which are not water soluble.

The compounds of the present invention are active against many fungi and particularly against Candida species. The antifungal properties may be illustrated with the minimum fungicidal concentration (MFC) determination against certain Candida organisms in a microbroth dilution assay carried out in a Yeast Nitrogen Base (DIFCO) medium with 1% dextrose (YNBD).

In a representative assay, compounds were solubilized in 100% dimethyl sulfoxide (DMSO) at an initial concentration of 5 mg/ml. Once dissolved, the drug stock was brought to a concentration of 512 µg/ml by dilution in water such that the final DMSO concentration was about 10 percent. The solution was then dispensed via a multichannel pipetter into the first column of a 96-well plate (each well containing 0.075 ml of YNBD), resulting in a drug concentration of 256 µg/ml. Compounds in the first column were diluted 2-fold across the rows yielding final drug concentration ranging from 256 µg/ml to 0.12 µg/ml.

Four-hour broth cultures of organisms to be tested were adjusted using a spectrophotometer at 600 nm to equal a 0.5 McFarland Standard. This suspension was diluted 1:100 in YNBD to yield a cell concentration of $1-5 \times 10^4$ colony forming units (CFU)/ml. Aliquots of the suspension (0.075 ml) were inoculated into each well of the microtiter plate resulting in a final cell inoculum of $5-25 \times 10^3$ CFU/ml and final drug concentrations ranging from 128 µg/ml to 0.06 µg/ml. Each assay included one row for drug-free control wells and one row for cell-free control wells.

After 24 hours of incubation, the microtiter plates were shaken gently on a shaker to resuspend the cells. The MIC-2000 inoculator was used to transfer a 1.5 microliter sample from each well of the 96-well microtiter plate to a single reservoir inoculum plate containing Sabouraud dextrose agar (SDA). The inoculated SDA plates were incubated for 24 hours at 35° C. and then read for minimum fungicidal concentration (MFC). MFC is defined as the lowest concentration of drug showing no growth or less than 4 colonies per spot. Compound I-A where $R_1 = OH$, $R_2 = H$, $R_3 = CH_2CH_2NH_2$, $R_4 = CH_3$, $R_5 = H$, $R_6 = OH$, $R^I$=dimethyltridecyl, $R^{II}$=H and $R^{III}$=H as the bishydrochloride salt had the following MFCs (1µg/ml):

Candida albicans (MY1055) <0.06
Candida tropicalis(MY1012) <0.06
Candida glabrata(MY1381) 0.25

The in vivo effectiveness of the compounds against fungi may be seen in the following assay.

Growth from an overnight SDA culture of *Candida albicans* MY 1055 was suspended in sterile saline and the cell concentration determined by hemacytometer count and the cell suspension adjusted to $3.75 \times 10^5$ cells/ml. Then 0.2 milliliter of this suspension was administered I.V. in the tail vein of mice so that the final inoculum is $7.5 \times 10^4$ cells/mouse.

The assay was then carried out by administering aqueous solutions of Compound I-A at various concentrations intraperitoneally (I.P.), twice daily (b.i.d.) for four consecutive days to 18 to 20 gram female DBA/2 mice, which previously had been infected with *Candida albicans* (MY 1055) in the manner described above. Distilled water was administered I.P. to *C. albicans* challenged mice as controls. After seven days, the mice were sacrificed by carbon dioxide gas, paired kidneys were removed aseptically and placed in sterile polyethylene bags containing 5 milliliters of sterile saline. The kidneys were homogenized in the bags, serially diluted in sterile saline and aliquots spread on the surface of SDA plates. The plates were incubated at 35° C. for 48 hours and yeast colonies enumerated for determination of colony forming units (CFU) per gram of kidneys. Compound I-A gave greater than 90% reduction of recoverable Candida CFUs at 0.02 mg/kg i.p. twice daily for four consecutive days.

The compounds of the present invention are also active against Aspergillus species. The in vivo effectiveness of the compounds against Aspergillus may be seen in the following assay.

Conidia of *Aspergillus fumigatus* MF 5668 were washed from the surface of several (3–4) 3–5 day SDA slant cultures with sterile saline plus 0.01% Tween 20. The conidia suspension was quantitated by hemacytometer count and adjusted to the appropriate concentration in sterile saline.

Female DBA/2 mice were challenged I.V. with $1.40 \times 10^6$ conidia/mouse. Within fifteen minutes after challenge, aqueous solutions of Compound I-A were administered intraperitoneally (I.P.) at various concentrations twice daily (b.i.d.) for a total of five days. The required dose of Compound I-A to increase the 28-day survival rate by at least 50% over untreated controls was 0.02 mg/kg.

A harmful and potentially fatal side reaction of a number of drugs including certain antibiotically active echinocandin compounds is red blood cell lysis. This is not seen in compounds having the present nuclei which is another advantage of the compounds of this invention.

The compounds of the present invention may also be useful for inhibiting or alleviating *Pneumocystis carinii* infections in immune-compromised patients. The efficacy of the compounds of the present invention for therapeutic or anti-infection purposes may be demonstrated in studies on immunosuppressed rats.

Sprague-Dawley rats (weighing approximately 250 grams) were iunmunosuppressed with dexamethasone in the drinking water (2.0 mg/L) and maintained on a low protein diet for seven weeks to induce the development of Pneumocystis pneumonia from a latent infection. Before drug treatment, two rats were sacrificed to confirm the presence of *Pneumocystis carinii* pneumonia (PCP). Five rats (weighing approximately 150 grams) were injected twice daily for four days subcutaneously (sc) with Compound I-A in 0.25 ml of vehicle (distilled water). A vehicle control was also carried out. All animals continued to receive dexamethasone in the drinking water and low protein diet during the treatment period. At the completion of the treatment, all animals were sacrificed, the lungs were removed and processed, and the extent of disease determined by microscopic analysis of stained slides. The prevention or reduction of cysts were seen in slides of the lungs of treated rats when compared with the number of cysts in the lungs of untreated controls or solvent controls. The results of this assay showed that Compound I-A reduced *P. carinii* cysts in 5 rats by at least 90 percent when dosed at 0.02 mg/kg with all rats surviving.

The outstanding properties are most effectively utilized when the compounds are formulated into novel pharmaceutical compositions with a pharmaceutically acceptable carrier according to the conventional pharmaceutical compounding techniques.

The novel compositions contain at least a therapeutic antifungal or antipneumocystis amount of the active compound. Generally, the composition contains at least 1% by weight of Compound I or II. Concentrate compositions suitable for dilutions prior to use may contain 90% or more by weight. The compositions include compositions suitable for oral, topical, parenteral (including intraperitoneal, subcutaneous, intramuscular, and intravenous), nasal, and suppository administration, or insufflation. The compositions may be prepacked by intimately mixing Compound I or II with the components suitable for the medium desired.

Compositions formulated for oral administration may be liquid or solid compositions. For liquid preparation, the therapeutic agent may be formulated with liquid carriers such as water, glycols, oils, alcohols, and the like, and for solid preparations such as capsules and tablets, with solid carriers such as starches, sugars, ethyl cellulose, calcium and sodium carbonate, calcium phosphate, kaolin, talc, lactose, generally with a lubricant such as calcium stearate, together with binders disintegrating agents and the like. Because of their ease in administration, tablets and capsules represent the most advantageous oral dosage form. It is especially advantageous to formulate the compositions in unit dosage form for ease of administration and uniformity of dosage. Compositions in unit dosage form constitute an aspect of the present invention.

Compositions may be formulated for injection and may take such forms as suspensions, solutions or emulsions in oily or aqueous vehicles such as 0.85 percent sodium chloride or 5 percent dextrose in water and may contain formulating agents such as suspending, stabilizing and/or dispersing agents. Buffering agents as well as additives such as saline or glucose may be added to make the solutions isotonic. The compound may also be solubilized in alcohol/propylene glycol or polyethylene glycol for drip intravenous administration. These compositions also may be presented in unit dosage form in ampoules or in multidose containers, preferable with added preservative. Alternatively, the active ingredients may be in powder form for reconstituting with a suitable vehicle prior to administration.

The term "unit dosage form" as used in the specification and claims refers to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampules or in multidose containers and the like. A unit dosage of the present invention will generally contain from 100 to 200 milligrams of one of the compounds.

When the compound is for antifungal use, any method of administration may be employed. For treating mycotic infections, oral or intravenous administration is usually employed.

When the compound is to be employed for control of Pneumocystis infections, it is desirable to directly treat lung and bronchi. For this reason inhalation methods are preferred. For administration by inhalation, the compounds of the present inventions are conveniently delivered in the form of an aerosol spray presentation from pressurized packs or nebulizers. The preferred delivery system for inhalation is a metered dose inhalation (MDI) aerosol, which may be formulated as a suspension or solution of Compound I or II in suitable propellants, such as fluorocarbons or hydrocarbons. Preferred propellants are those which do not damage the ozone layer.

Although the compounds of the present invention may be employed as tablets, capsules, topical compositions, insufflation powders, suppositories and the like, the solubility of the compounds of the present invention in water and aqueous media render them adaptable for use in injectible formulations and also in liquid compositions suitable for aerosol sprays.

The following examples illustrate the invention but are not to be construed as limiting. All temperatures are in degrees centigrade (°C.) unless indicated otherwise.

EXAMPLE 1

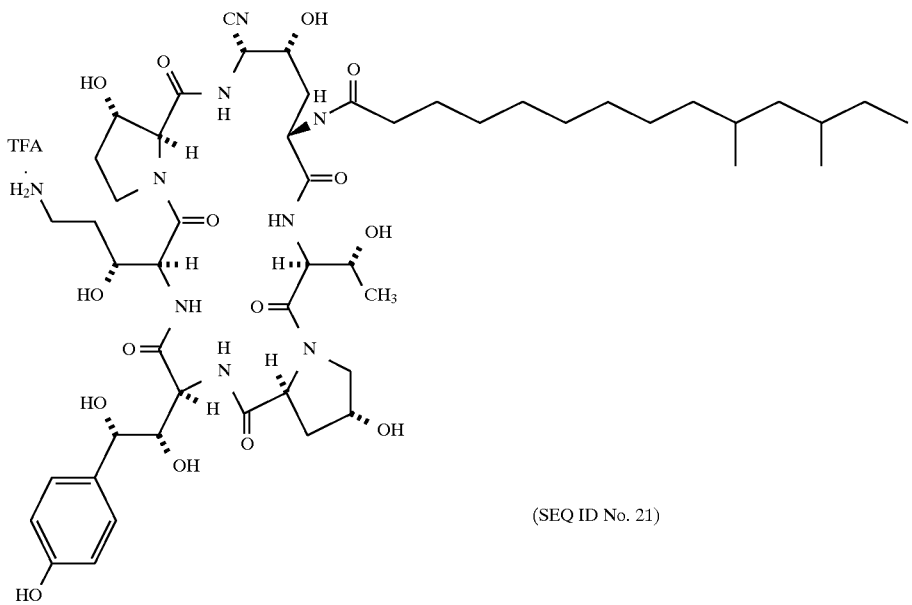

(SEQ ID No. 21)

Part A: Preparation of Thioether Intermediate

Trifluoroacetic acid (0.4 ml, 5.3 mmol) was added to a solution of

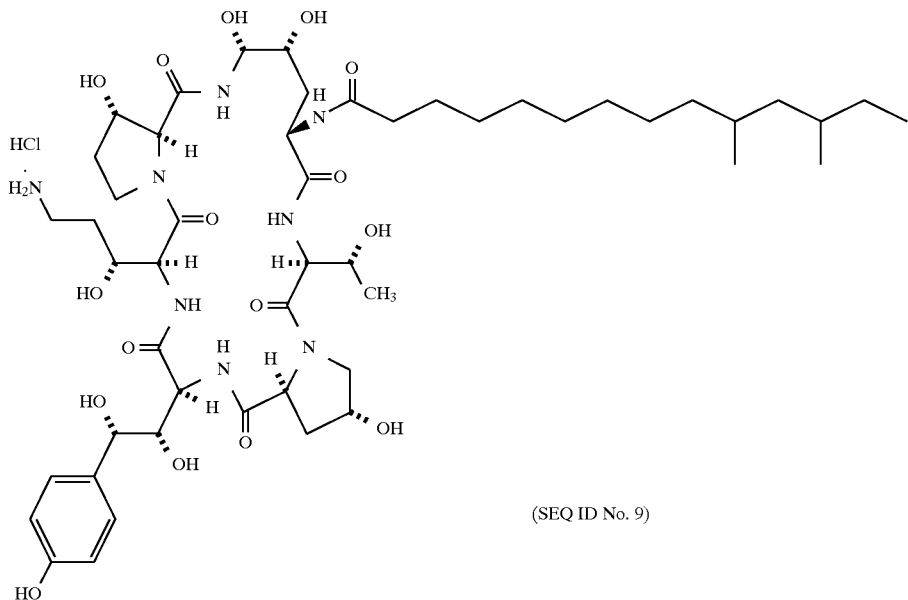

(SEQ ID No. 9)

(22.9 g, 21.1 mmol) and 2-aminoethanethiol hydrochloride (47.9 g, 422 mmol) in 100 ml of anhydrous N,N-dimethylformamide at 60° C. After a period of 4 h, the reaction mixture was cooled to room temperature and diluted with 400 ml of $H_2O$. Filtration of the resulting solution was followed by pump-injection of the filtrate onto a Waters Delta Pak C18-100 Å radial cartridge (47 mm×30 cm) at a rate of 50 ml/min. Elution with 25–30% $CH_3CN/H_2O$ (0.1% $CF_3COOH$) in one 5% step gradient gave, after lyophilization of the appropriate fractions, 6.5 g of the nor-thioether and 6.8 g of the epi-thioether as bistrifluoroacetate salts. By analytical HPLC (Zorbax RX-C18, 40% $CH_3CN/H_2O$ (0.1% $CF_3COOH$), uv at 210 nm), the thioethers were sufficiently pure (>80%) for conversion to sulfone as described below. Rechromatography of the individual isomers followed by ion exchange on a Bio-Rad AG2-X8 ($Cl^-$) column eluting with $H_2O$ provided, after lyophilization, pure bishydrochlorides as amorphous solids. Nor-thioether: $^1H$ NMR (400 MHz, $CD_3OD$) d 1.17 (d, J=6.2 Hz, 3H), 2.9 (m, 2H), 3.06 (t, J=7.2 Hz, 2H), 3.20 (t, J=6.7 Hz, 2H), 4.91 (d, J=5.8 Hz, 2H), 4.99 (d, J=3.4 Hz), 5.27 (d, J=2.1 Hz, 1H), 6.74 (d, J=8.6 Hz, 2H), 7.11 (d, J=8.6 Hz, 2H); FAB-MS (Li) m/z 1117 $(MH+Li)^+$. Epi-thioether: $^1H$ NMR (400 MHz, $CD_3OD$) d 2.23 (m, 3H), 2.41 (dd, J=7.4 and 13.1 Hz, 1H), 2.92 (m, 2H), 3.11 (m, 2H), 3.06–3.29 (m, 4H), 4.01 (m, 1H), 4.10 (d, J=4.6 Hz, 1H), 4.64 (dd, J=7.2 and 10.9 Hz, 1H), 4.69 (br s, 1H), 4.95 (d, J=3.9 Hz, 1H), 6.76 (d, J=8.6 Hz, 2H), 7.14 (d, J=8.6 Hz, 2H); FAB-MS (Li) m/z 1117 $(MH+)^+$.

Part B: Preparation of Sulfone

To a stirred solution of the epi-thioether from Part A (6.5 g, ~70% pure) in 55 ml of 1:1 acetonitrile/water at 25° C. was added OXONE® (3.1 g). After a period of 15 min, analysis by C18-HPLC showed the conversion to a more polar product to be complete. The reaction mixture was lyophilized to provide the crude sulfone which was used in the subsequent step without purification.

Part C: Preparation of Nitrile

A solution of the epi-sulfone bistrifluoroacetate from Part B (2.3 g, 73% pure, 1.23 mmol corrected for purity) in 123 ml of 0.5M lithium cyanide in N,N-dimethylformamide was stirred at 25° C. for a period of 15 minutes. HPLC analysis [RP-C18, 45% $CH_3CN/H_2O$ (0.1% $CF_3COOH$)] of the reaction mixture indicated complete conversion to two less polar products. The reaction mixture was diluted with water (400 ml) and the resulting heterogeneous mixture was loaded onto a reverse-phase flash column (C18, 30 g) packed in 20% $CH_3CN/H_2O$. Elution with $H_2O$ (200 ml) was followed by 20–70% $CH_3CN/H_2O$ (0.1% $CF_3COOH$) in 10% step-gradients collecting 100 ml at each step. The insoluble cake remaining at the top of the column was removed and dissolved in 70% $CH_3CN/H_2O$ (0.1% $CF_3COOH$). This solution was combined with the product-containing fractions and lyophilized to give 1.5 g of crude nitriles. Reverse-phase HPLC of this material [C18, 30–45% $CH_3CN/H_2O$ (0.1% $CF_3COOH$) in 5% step-gradients] gave, after lyophilization of the appropriate fractions, 220 mg (21%) of the nor-nitrile and 270 mg (36%) of the epi-nitrile as the trifluoroacetate salts. Nor-nitrile: $^1H$ NMR (500 MHz, $CD_3OD$) d 1.16 (d, J=6.2 Hz, 3H), 1.60 (m, 2H) 1.81 (m, 1H), 2.44 (dd, J=7.0 and 13.0 Hz, 1H), 3.06 (m, 2H), 3.83 (m, 3H), 3.95 (dd, J=3.2 and 11.2 Hz, 1H), 4.03 (m, 1H), 4.43 (m, 1H), 4.54 (dd, J=7.1 and 11.7 Hz, 1H), 4.60 (dd, J=3.4 and 6.2 Hz, 1H), 4.80 (d, J=2.3 Hz, 1H), 4.97 (d, J=3.2 Hz, 1H), 6.75 (d, J=8.5 Hz, 2H), 7.11 (d, J=8.5 Hz, 2H); ESI-MS (M+H)$^+$=1060.7. Epi-nitrile: $^1H$ NMR (500 MHz, $CD_3OD$) d 1.23 (d, J=6.0 Hz), 2.05 (m, 1H), 2.42 (dd, J=6.6 and 13.5 Hz, 1H), 3.10 (t, J=7.4 Hz, 2H), 3.76 (m, 3H), 3.94 (dd, J=3.2 and 11.2 Hz, 1H), 4.00 (d, J=5.5 Hz, 1H), 4.11 (m, 1H), 4.62 (dd, J=3.9 and 11.4 Hz, 1H), 4.81 (d, J=6.9 Hz, 1H), 4.88 (d, J=2.8 Hz, 1H), 6.75 (d, J=8.5 Hz, 2H), 7.11 (d, J=8.5 Hz, 2H); ESI-MS (M+H)$^+$=1060.7.

EXAMPLE 2

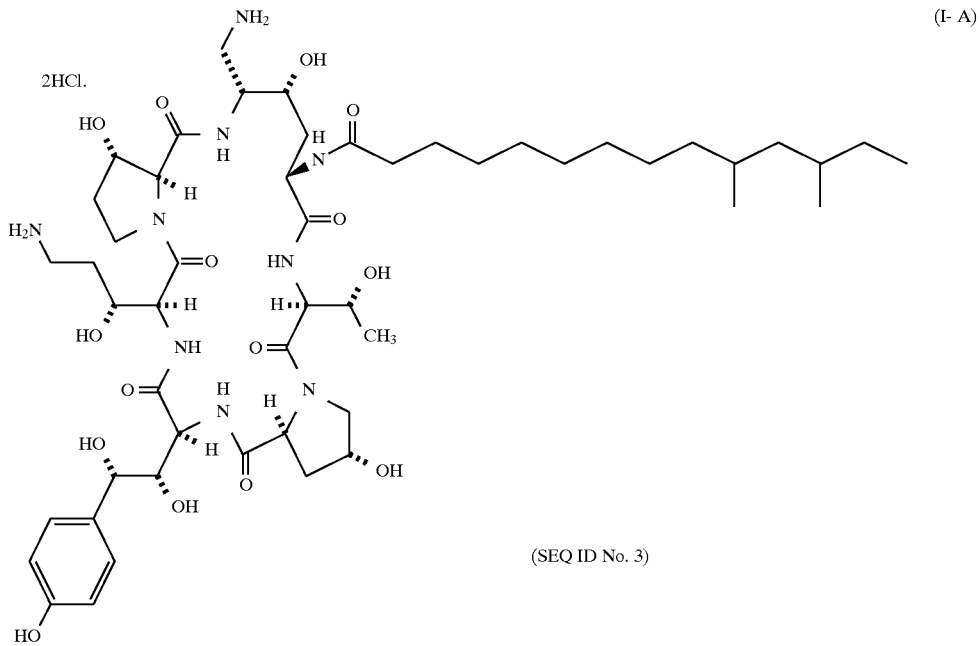

(I-A)

(SEQ ID No. 3)

Sodium borohydride (91.2 mg, 2.41 mmol) was added in portions to a solution of $CoCl_2 \cdot 6H_2O$ (115 mg, 0.482 mmol) and the nor-nitrile (Example 1, 283 mg, 0.241 mmol) in MeOH (9 ml). The ensuing exothermic reaction produced a precipitate while evolving copious quantities of hydrogen. HPLC analysis (Zorbax RX-C18, 4.6 mm×25 cm; 45% $CH_3CN/H_2O$ (0.1% $CF_3COOH$) at 1.5 ml/min; uv detection at 210 and 277 nm) after 10 minutes indicated 70% conversion to a more polar product ($T_R$=3.0 min). 2N $CF_3COOH$ (7.8 ml) was added to the reaction mixture and stirring was continued for a period of 30 minutes, resulting in the dissolution of the precipitate. The mixture was diluted with $H_2O$ (40 ml) and then filtered through a packed bed of diatomaceous earth. The filtrate was pump-injected onto a Zorbax RX-C18 HPLC column (21.2 mm×25 cm) in 30% $CH_3CN/H_2O$ (0.1% $CF_3COOH$). Elution with 30–45% $CH_3CN/H_2O$ (0.1% $CF_3COOH$) in 5% step-gradients at a flow rate of 10 ml/min followed by lyophilization of the appropriate fractions gave 93 mg of the bisamine as the trifluoroacetate. The bistrifluoroacetate was dissolved in $H_2O$ (10 ml) and the solution loaded onto a Bio-Rad AG2-X8 (Cl$^-$) polyprep column (2 ml resin bed). Gravity elution with water (3×10 ml) followed by lyophilization of the eluate gave 80 mg of the above compound. Yield (corrected)=34%. $^1H$ NMR (500 MHz, $CD_3OD$) d 1.18 (d, J=6.2 Hz, 3H), 1.80 (m, 1H) 1.92–2.12 (m, 4H), 2.18–2.36 (m, 4H), 2.43 (dd, J=6.5 and 12.9 Hz, 1H), 3.07 (m, 2H), 3.16 (dd, J=5.4 and 13.2 Hz, 1H), 3.23 (dd, J=3.9 and 13.2 Hz, 1H), 3.80 (m, 3H), 3.99 (dd, J=3.1 and 11.1 Hz, 1H), 4.02–4.10 (m, 2H), 4.15 (m, 1H), 4.19 (dd, J=1.5 and 8.1 Hz, 1H), 4.51–4.65 (m, 4H), 4.97 (d, J=3.2 Hz, 1H), 6.75 (d, J=8.6 Hz, 2H), 7.11 (d, J=8.6 Hz, 2H); ESI-MS m/z 1064.6 (M+H)$^+$, 532.9 (M+H)$^{++}$.

EXAMPLE 3

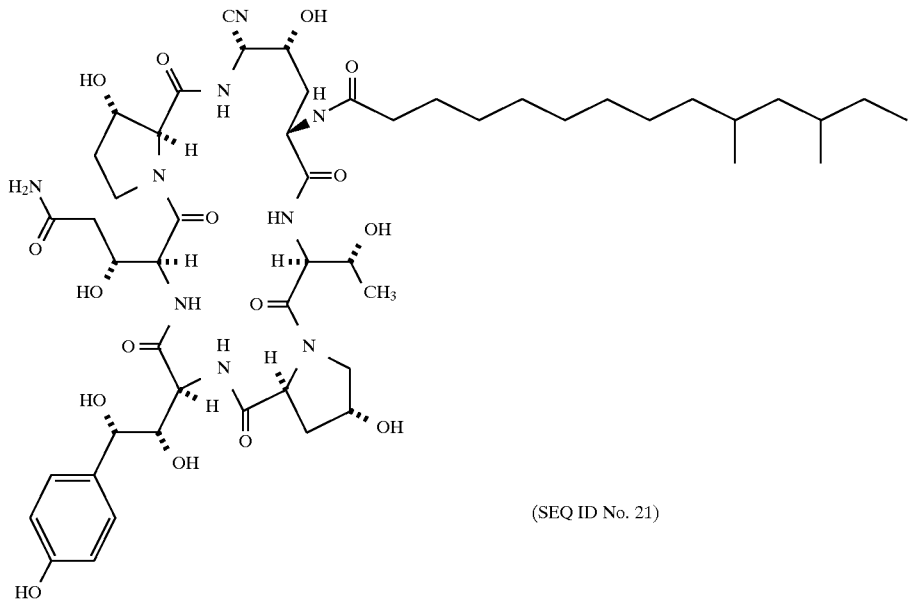

(SEQ ID No. 21)

Part A: Preparation of Thioether Intermediate (1S)-(+)-10-Camphorsulfonic acid (2.39 g, 10.3 mmol) was added to a solution of

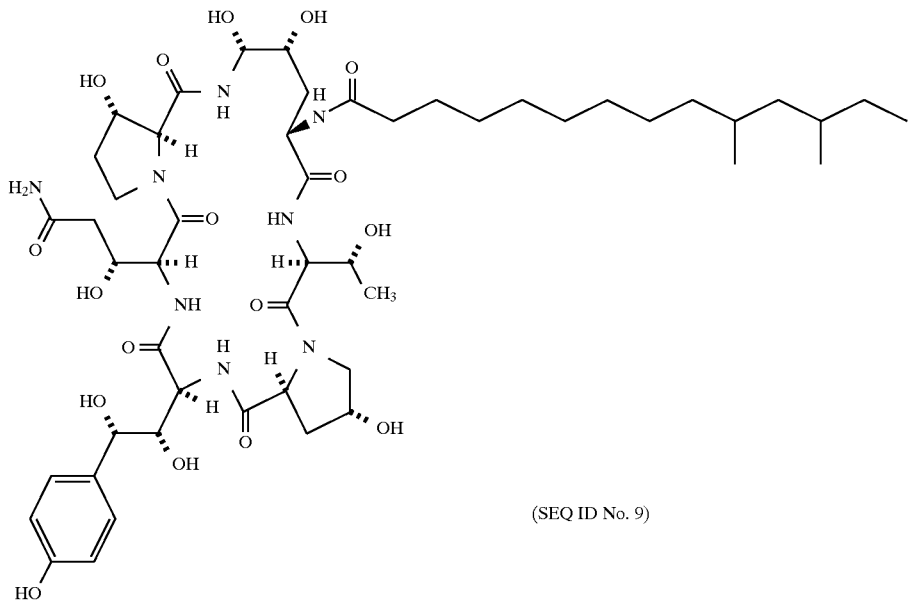

(SEQ ID No. 9)

(11.0 g, 10.3 mmol) and 2-aminoethanethiol hydrochloride (53 g, 467 mmol) in 200 ml of anhydrous N,N-dimethylformamide at 25° C. After a period of 72 h, the reaction mixture was diluted with $H_2O$ (400 ml) and loaded onto a reverse-phase flash column (C18, 110 g) packed in 10% $CH_3CN/H_2O$. Elution with 10–60% $CH_3CN/H_2O$ in 10% step-gradients followed by lyophilization of the product-containing fractions (40–50% $CH_3CN/H_2O$) gave 8.7 g of impure thioethers. Preparative HPLC of this mixture (Waters Delta Pak C18-100 Å radial cartridge, 47 mm×30 cm) eluting with 20–40% $CH_3CN/H_2O$ (0.1% $CF_3COOH$) at 50 ml/min in 10% step gradients gave, after lyophilization of the appropriate fractions, 2.0 g of the nor-thioether (yield=16%, HPLC purity >95%) and 5.2 g of the epi-thioether (yield=40%, HPLC purity ca. 85%) as the trifluoroacetate salts. Nor-thioether: $^1$H NMR (400 MHz, $CD_3OD$) d 1.14 (d, J=6.2 Hz, 3H), 2.83 (m, 2H), 5.44 (d, J=1.8 Hz, 1H); FAB-MS (Li) m/z 1131 (M+H+Li)$^+$. Epi-thioether: $^1$H NMR (400 MHz, $CD_3OD$) d 1.34 (d, J=6.3 Hz, 3H), 2.89 (m, 2H), 4.72 (d, J=4.9 Hz, 1H); FAB-MS (Li) m/z 1131 (M+H+Li)$^+$.

Part B: Preparation of Sulfone

In a manner similar to that described in Example 1, Part B, the epi-sulfone was prepared from the epi-thioether.

Part C: Preparation of Nitrile

A solution of the epi-sulfone (1.0 g) in 79 ml of 0.5M lithium cyanide in N,N-dimethylformamide was stirred at 25° C. for a period of 10 minutes. HPLC analysis [RP-C18, 50% $CH_3CN/H_2O$ (0.1% $CF_3COOH$)] of the reaction mixture indicated complete conversion to two less polar products. The reaction mixture was diluted with water (240 ml) and the resulting solution was loaded onto a reverse-phase flash column (C18, 20 g) packed in 10% $CH_3CN/H_2O$. Elution with 20–70% $CH_3CN/H_2O$ in 10% step-gradients collecting 100 ml at each step followed by lyophilization of the product-containing fractions gave 610 mg of crude nitriles. Reverse-phase HPLC of this mixture (C18, 45–55% $CH_3CN/H_2O$ in 5% step-gradients) gave, after lyophilization of the appropriate fractions, 87 mg (yield=10%, HPLC purity @ 210 nm=97%) of the nor-nitrile and 190 mg (yield=22%, HPLC purity @ 210 nm=99%) of the epi-nitrile as white amorphous solids. Nor-nitrile: $^1$H NMR (500 MHz, $CD_3OD$) d 1.14 (d, J=6.2 Hz, 3H), 1.59 (m, 2H) 1.93–2.08 (m, 3H), 2.15–2.27 (m, 5H), 2.43 (m, 1H), 2.47 (dd, J=9.5 and 15.4 Hz, 1H), 2.74 (dd, J=3.8 and 15.4 Hz, 1H), 3.78 (m, 2H), 3.97 (m, 2H), 4.18 (m, 1H), 4.39 (dd, J=4.4 and 12.8 Hz, 1H), 4.55 (m, 3H), 4.98 (m, 2H), 5.07 (d, J=4.1 Hz, 1H), 6.74 (d, J=8.5 Hz, 2H), 7.12 (d, J=8.5 Hz, 2H); ESI-MS $(M+H)^+$=1074.5. Epi-nitrile: $^1$H NMR (500 MHz, $CD_3OD$) d 1.59 (m, 2H), 1.76 (m, 1H), 1.98 (m, 1H), 2.07 (m, 2H), 2.22 (m, 3H), 2.39 (dd, J=7.4 and 13.2 Hz, 1H), 2.45 (dd, J=8.0 and 15.1 Hz, 1H), 2.57 (dd, J=5.4 and 15.1 Hz, 1H), 4.02 (m, 1H), 4.07 (d, J=4.6 Hz, 1H), 4.31 (dd, J=1.9 and 7.9 Hz, 1H), 4.36 (m, 4H), 4.55 (m, 3H), 4.63 (dd, J=7.4 and 10.6 Hz), 5.04 (d, J=3.4 Hz), 6.76 (d, J=8.5 Hz, 2H), 7.14 (d, J=8.5 Hz, 2H); ESI-MS $(M+H)^+$=1074.4.

15.4 Hz, 1H), 3.15 (d, J=5.7 Hz, 2H), 3.80 (m, 2H), 3.96 (m, 2H), 4.06 (m, 1H), 4.17 (m, 1H), 4.23 (dd, J=1.4 and 7.8 Hz, 1H), 4.57 (m, 4H), 5.00 (d, J=3.4 Hz, 1H), 5.06 (d, J=5.0 Hz, 1H), 6.74 (d, J=8.6 Hz, 2H), 7.12 (d, J=8.6 Hz, 2H); ESI-MS m/z 1078.7 $(M+H)^+$, 531.1 $(M—H_2O+H)^{++}$.

EXAMPLE 5

EXAMPLE 4

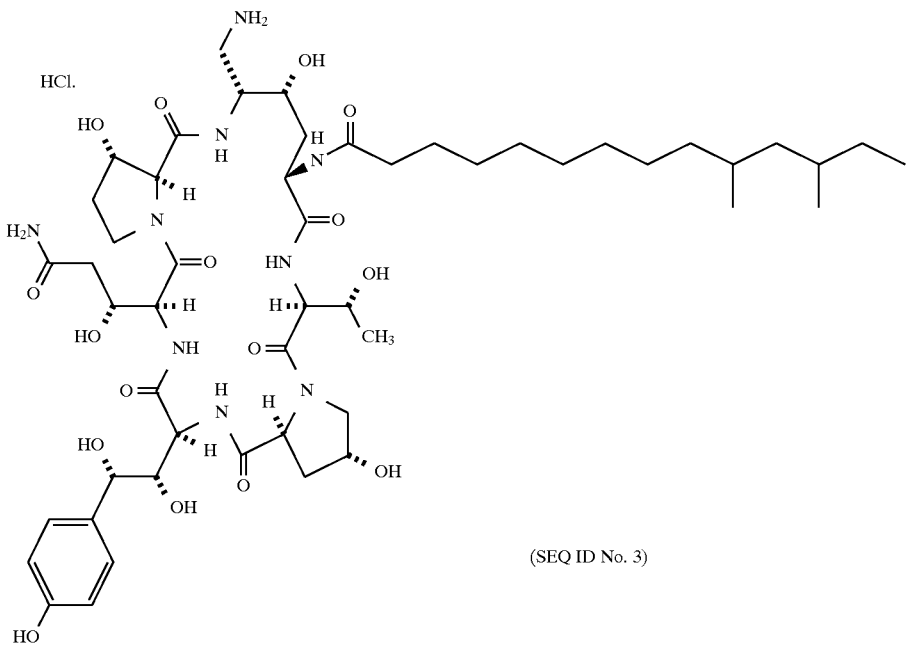

(SEQ ID No. 3)

In a manner similar to that described in Example 2, the nor-nitrile from Example 3 was reduced to the amine shown above. Yield=44% ($CF_3COOH$ salt). $^1$H NMR of hydrochloride salt (500 MHz, $CD_3OD$) d 1.16 (d, J=6.2 Hz, 3H), 1.9–2.1 (m, 3H), 2.23 (m, 4H), 2.42 (dd, J=6.6 and 12.6 Hz, 1H), 2.48 (dd, J=9.4 and 15.4 Hz, 1H), 2.75 (dd, J=3.7 and

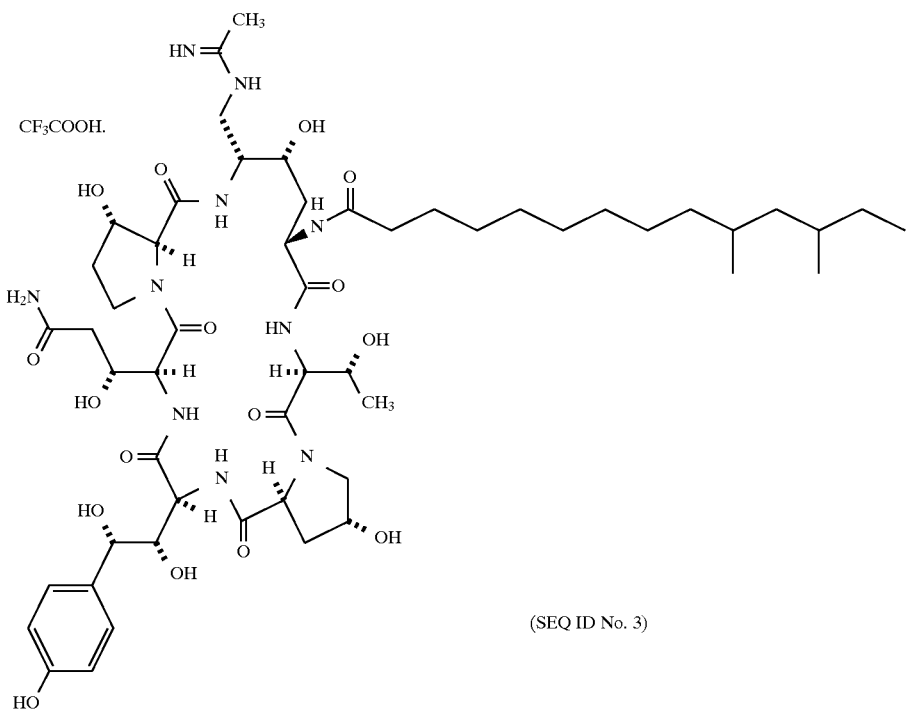

(SEQ ID No. 3)

To a stirred solution of the amine trifluoroacetate from Example 4 (153 mg, 0.128 mmol) and 1N sodium hydroxide (130 μl, 0.130 mmol) in water (5 ml) and N,N-dimethylformamide (5 ml) is added ethylacetimidate hydrochloride (160 mg, 1.29 mmol). After a period of 18 h at pH 8.5, trifluoroacetic acid is added to pH 7. Reverse-phase (C18) flash column chromatography of the neutralized reaction mixture, eluting with acetonitrile/water, is followed by lyophilization of the product-containing fractions. Preparative reverse-phase (C18) HPLC of this material, eluting with acetonitrile/water (0.1% $CF_3COOH$), is followed by lyophilization of the product-containing fractions to give the acetamidine as the trifluoroacetate salt: $C_{55}H_{87}F_3N_{10}O_{18}$, formula weight=1233.36.

EXAMPLE 6

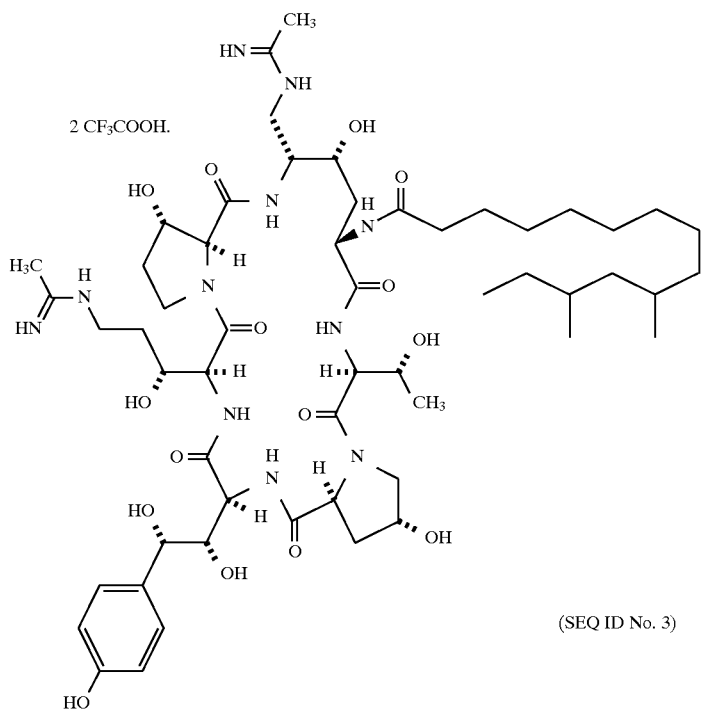

(SEQ ID No. 3)

In a manner similar to that described in Example 5, bisamine from Example 2 is converted to the bisacetamidine shown above: $C_{59}H_{93}F_6N_{11}O_{19}$, formula weight=1374.45.

EXAMPLE 7

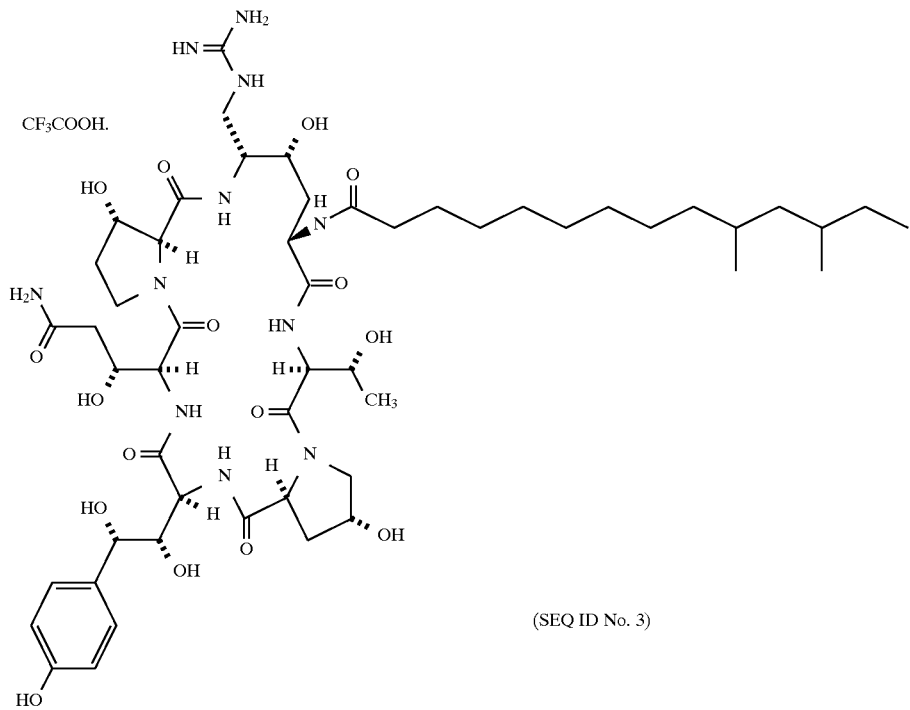

(SEQ ID No. 3)

To a stirred solution of the amine trifluoroacetate from Example 4 (163 mg, 0.137 mmol) and 1M sodium bicarbonate (150 µl, 0.150 mmol) in absolute methanol (5 ml) is added aminoiminomethanesulfonic acid (30 mg, 0.242 mmol). After a period of 1.5 h, the solvent is removed in vacuo. Preparative reverse-phase HPLC (C18) of the residue, eluting with acetonitrile/water (0.1% trifluoroacetic acid), is followed by lyophilization of the product-containing fractions to give the guanidine trifluoroacetate: $C_{54}H_{86}F_3N_{11}O_{18}$, formula weight=1234.35.
EXAMPLE 8
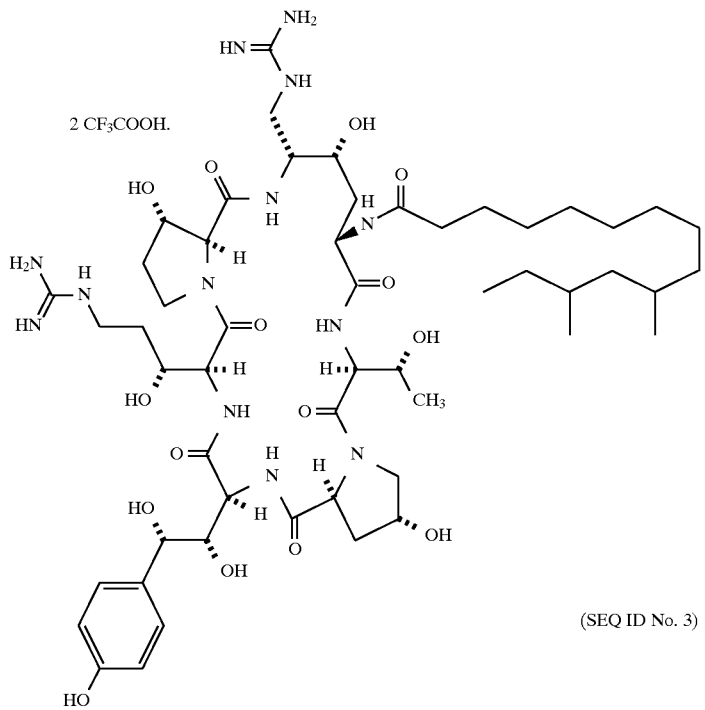
(SEQ ID No. 3)
In a manner similar to that described in Example 7, bisamine from Example 2 is converted to the bisguanidine shown above: $C_{57}H_{91}F_6N_{13}O_{19}$, formula weight=1376.43.
EXAMPLE 9

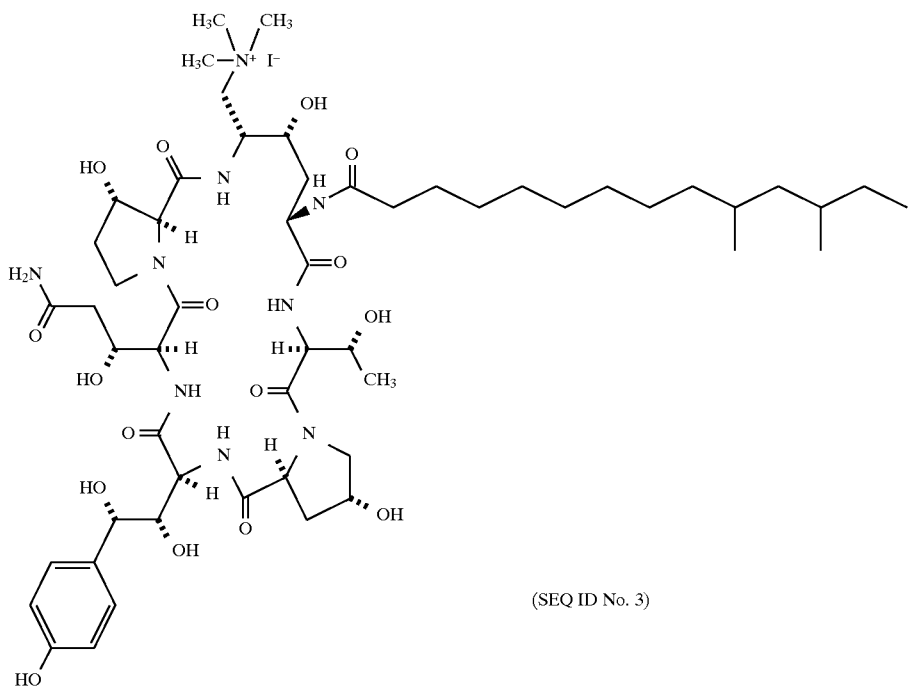

(SEQ ID No. 3)

To a stirred solution of the amine trifluoroacetate from Example 4 (149 mg, 0.125 mmol) in N,N-dimethylformamide (10 ml) and 1M sodium bicarbonate (2 ml, 2 mmol) is added iodomethane (2 ml, 32.1 mmol). The reaction mixture is stirred for a period of 18 h. The mixture is diluted with water (2×) and chromatographed. Reverse-phase (C18) flash column chromatography eluting with acetonitrile/water is followed by lyophilization of the product-containing fractions to provide the trimethylammonium iodide: $C_{54}H_{90}IN_9O_{16}$, formula weight=1248.27.

EXAMPLE 10

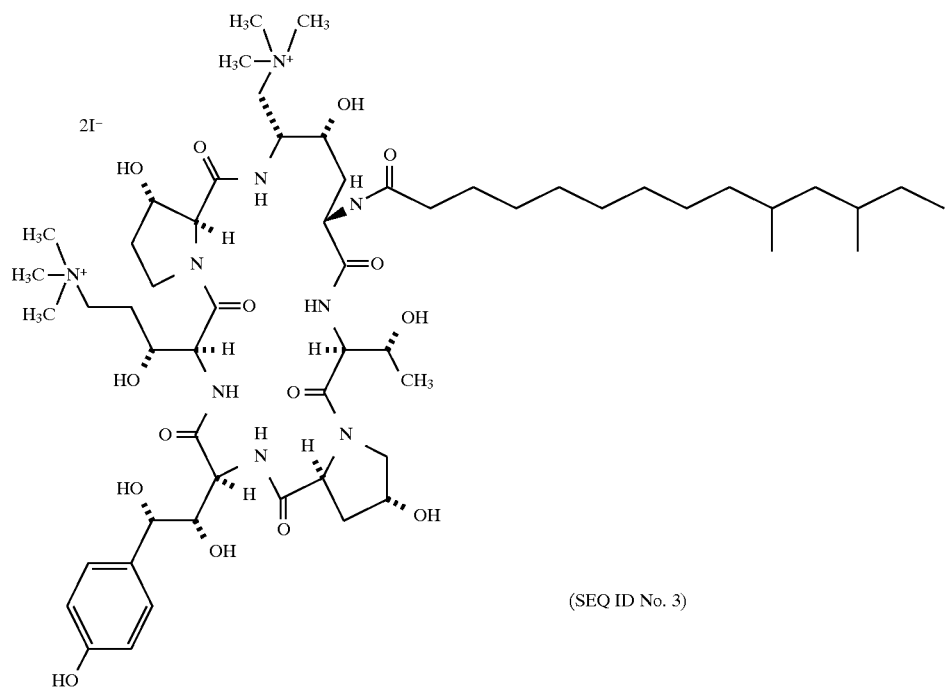

(SEQ ID No. 3)

In a manner similar to that described in Example 9, bisamine from Example 2 is converted to the bistrimethylammonium iodide shown above: $C_{57}H_{99}I_2N_9O_{15}$, formula weight=1404.28.

EXAMPLE 11

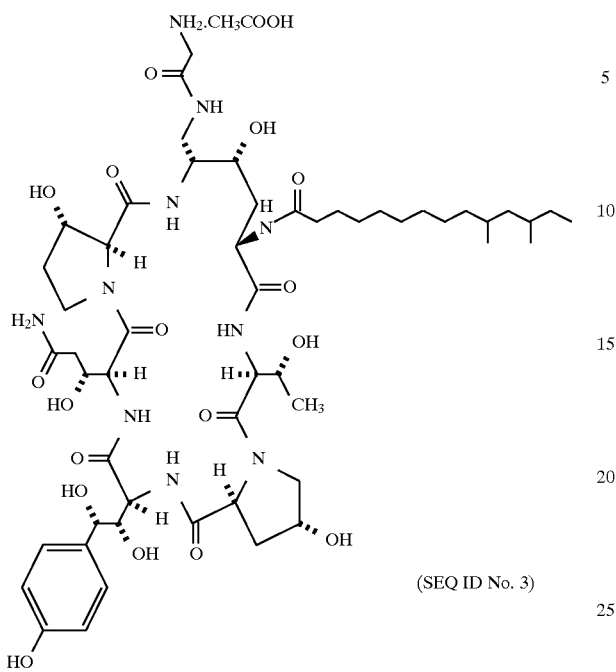

(SEQ ID No. 3)

Part A: Preparation of CBZ-Glyamide

The amine trifluoroacetate from Example 4 (215 mg, 0.180 mmol) is dissolved in N,N-dimethylformamide (2 ml). To this solution 1M sodium bicarbonate (200 μl, 0.200 mmol) and pentafluorophenyl N-benzyloxycarbonylglycinate (106 mg, 0.270 mmol) is added. After 1 h, the reaction mixture is diluted with water (2×). Isolation by reverse-phase (C18) flash column chromatography eluting with acetonitrile/water gives, after lyophilization of the product-containing fractions, the N-CBZ glyamide: $C_{61}H_{92}N_{10}O_{19}$, formula weight=1269.47.

Part B: Deprotection

A solution of the N-CBZ glyamide from Part A in glacial acetic acid is hydrogenated under balloon pressure in the presence of 10% Pd/C for a period of 1.5 hours. The reaction mixture is filtered to remove the catalyst and the filtrate is lyophilized to give the glyamide as the acetate salt: $C_{55}H_{90}N_{10}O_{19}$, formula weight=1195.39.

EXAMPLE 12

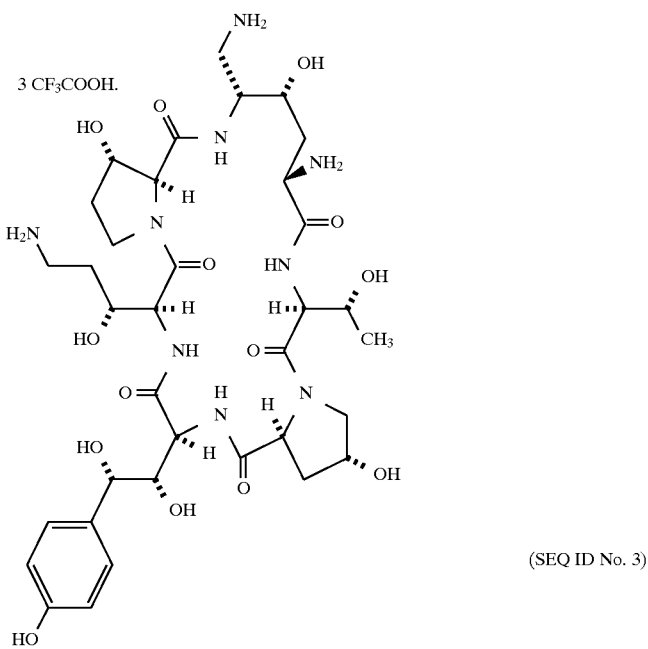

(SEQ ID No. 3)

Part A. Preparation of the Deacylating Enzyme

*P. acidovorans* $ATCC_{53942}$, maintained on Luria-Bertani medium agar slants was used to produce the deacylation enzyme.

A seed culture was prepared by inoculating a 50-ml portion of Luria-Bertani medium in a 250 ml flask with a loopful of the bacterium and the culture was incubated for about 24 hours at 27° C. with constant shaking. Cells for the deacylation were grown by inoculating 15 liters of Luria-Bertani medium in a stirred fermentor with 30 ml of the seed culture and incubating with agitation of 400 rpm and aeration at 7.5 liters/min. at 28° C. for 20 to 24 hours. The cells were washed with 50 mM potassium phosphate buffer, pH 7.5 and resuspended in about 4 liters of the same buffer. The suspension was equilibrated to 37° C. to obtain the deacylating enzyme.

Part B. Deacylation

The bisamine from Example 2.(3.5 g) is dissolved in 900 ml of distilled water and added slowly over a 1 hour period to 2 liters of the suspension of *P. acidovorans* cells from Part A. The resulting mixture is maintained at 37° C. while stirring at about 300 rpm without aeration. After 24 hours, the deacylation mixture is cleared of *P. acidovorans* cells by centrifugation and the nucleus is isolated from the supernatant by C18-high pressure liquid chromatography. Elution with 0–2% $CH_3CN/H_2O$ containing 0.1% $CF_3COOH$ in 0.5% step gradients is followed by lyophilization of the nucleus-containing fractions to give the deacylated product shown above as the tristrifluoroacetate salt: $C_{41}H_{58}F_9N_9O_{20}$, formula weight=1167.95.

EXAMPLE 13

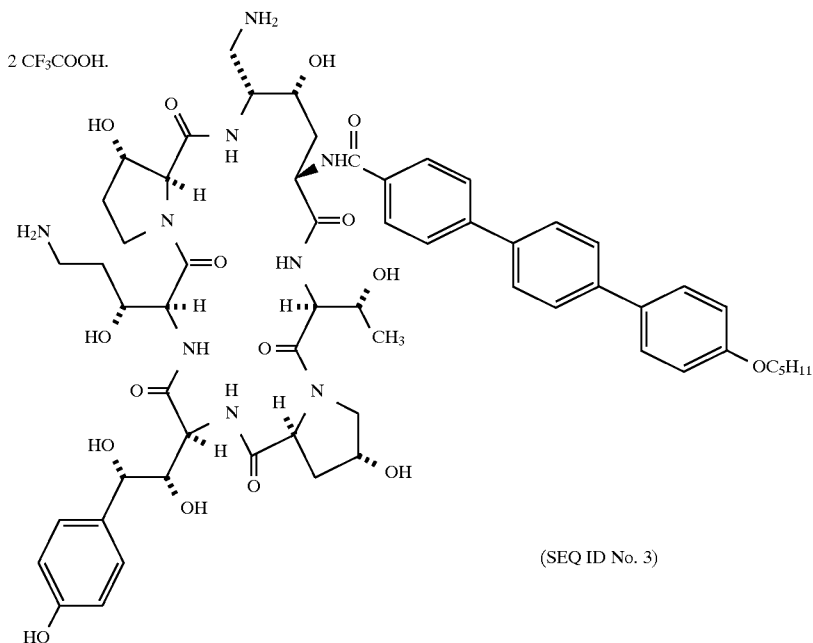

(SEQ ID No. 3)

Part A: Selective Protection and Reacylation of the Nucleus

To a stirred solution of the nucleus (102 mg, 0.087 mmol) from Example 12 and benzyl 4-nitrophenylcarbonate (47.4 mg, 0.173 mmol) in anhydrous N,N-dimethylformamide (3.5 ml) is added triethylamine (48.4 μl, 0.347 mmol). The reaction mixture is stirred for a period of 1 hour. 4-(n-Pentoxyphenyl)-4'-pentafluorophenoxycarbonylbiphenyl (46 mg, 0.087 mmol) prepared as described in Preparation of Starting Materials is added and stirring is continued for a period of 60 hours. The reaction mixture is diluted with water (3.5 ml) and the product is isolated by C18 solid-phase extraction eluting initially with $CH_3CN/H_2O$ and then $CH_3OH$. Concentration of the product-containing $CH_3OH$ fractions as determined by analytical HPLC gives crude bis-CBZ pentoxyterphenyl intermediate: $C_{75}H_{89}N_9O_{20}$, molecular weight=1436.59.

Part B. Deprotection

A solution of the crude bis-CBZ terphenyl intermediate from Part A in methanol (10 ml) and glacial acetic acid (4 ml) is hydrogenated under balloon pressure in the presence of 10% Pd/C for a period of 1.75 hours. The reaction mixture is filtered through a bed of diatomaceous earth to remove the catalyst, rinsing with MeOH. The filtrate is concentrated in vacuo. Preparative C18-HPLC of the residue, loaded in mobil phase containing sufficient $CH_3OH$ to fully solubilize, eluting with $CH_3CN/H_2O$ containing 0.1% $CF_3COOH$ is followed by lyophilization of the product-containing fractions as determined by analytical HPLC to give the pentoxyterphenyl compound shown above as the bistrifluoroacetate salt: $C_{63}H_{79}F_6N_9O_{20}$, formula weight=1396.37.

EXAMPLE 14

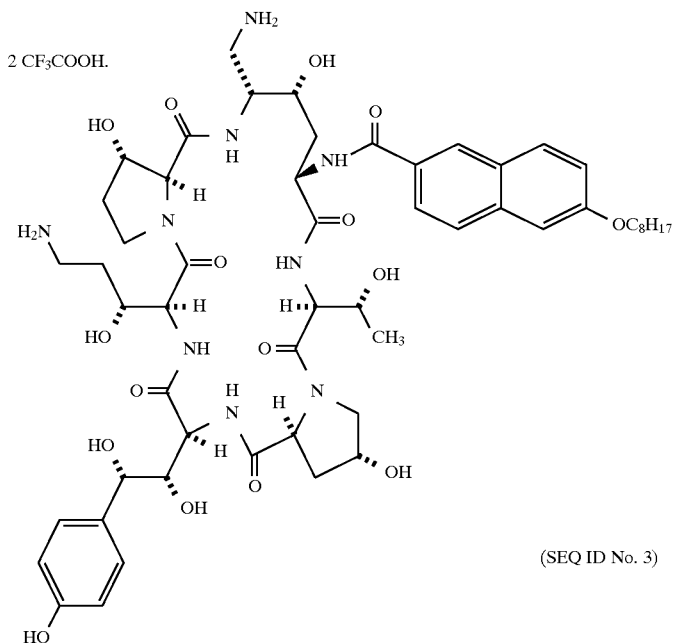

(SEQ ID No. 3)

Part A: Selective Protection and Reacylation of the Nucleus

To a stirred solution of the nucleus (102 mg, 0.087 mmol) from Example 12 and benzyl 4-nitrophenylcarbonate (47.4 mg, 0.173 mmol) in anhydrous N,N-dimethylformamide (3.5 ml) is added triethylamine (48.4 μl, 0.347 mmol). The reaction mixture is stirred for a period of 1 hour. Pentafluorophenyl 6-octyloxy-2-naphthoate (39 mg, 0.087 mmol) prepared as described in Preparation of Starting Materials is added and stirring is continued for a period of 60 hours. The reaction mixture is diluted with water (3.5 ml) and the product is isolated by C18 solid-phase extraction eluting initially with $CH_3CN/H_2O$ and then $CH_3OH$. Concentration of the product-containing $CH_3OH$ fractions as determined by analytical HPLC gives crude bis-CBZ octyloxynaphthoyl intermediate: $C_{70}H_{89}N_9O_{20,}$ molecular weight=1376.54.

Part B. Deprotection

A solution of the crude bis-CBZ octyloxynaphthoyl intermediate from Part A in methanol and glacial acetic acid (2.5:1) is hydrogenated under balloon pressure in the presence of 10% Pd/C for a period of 1.75 hours. The reaction mixture is filtered through a bed of diatomaceous earth to remove the catalyst, rinsing with MeOH. The filtrate is concentrated in vacuo. Preparative C18-HPLC of the residue, loaded in mobil phase containing sufficient $CH_3OH$ to fully solubilize, eluting with $CH_3CN/H_2O$ containing 0.1% $CF_3COOH$ is followed by lyophilization of the product-containing fractions as determined by analytical HPLC to give the octyloxynaphthoyl compound shown above as the bistrifluoroacetate salt: $C_{58}H_{79}F_6N_9O_{20}$, formula weight=1336.32.

EXAMPLE 15

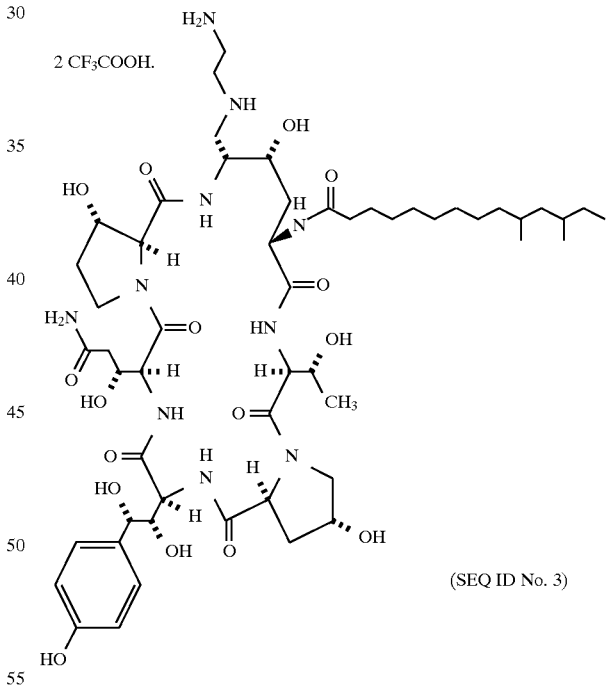

(SEQ ID No. 3)

Part A: Alkylation

To a vigorously stirred solution of the amine trifluoroacetate from Example 4 (149 mg, 0.125 mmol) and N,N-diisopropylethylamine (16.2 mg, 0.125 mmol) in N,N-dimethylformamide (10 ml) is added dropwise a solution of 2-(benzyloxycarbonyl)-aminoethyl bromide (32.3 mg, 0.125 mmol) in N,N-dimethylformamide (5 ml). The reaction mixture is stirred until C18 HPLC analysis with $CH_3CN/H_2O$ indicates complete consumption of starting material. The mixture is diluted with water and chromatographed. Reverse-phase (C18) flash column chromatography eluting with $CH_3CN/H_2O$ (0.1% $CF_3COOH$) is followed by lyophilization of the product-containing fractions to provide the (benzyloxycarbonyl)-aminoethyl intermediate: $C_{61}H_{94}N_{10}O_{18}$, formula weight=1255.49.

Part B: Deprotection

A solution of the CBZ protected intermediate from Part A in glacial acetic acid is hydrogenated under balloon pressure in the presence of 10% Pd/C for a period of 1.5 hours. The reaction mixture is filtered to remove the catalyst and the filtrate is lyophilized. Preparative C18 HPLC of the lyophilizate eluting with $CH_3CN/H_2O$ (0.1% $CF_3COOH$) provides the bisamine shown above as the ditrifluoroacetate salt: $C_{57}H_{90}F_6N_{10}O_{20}$, formula weight=1349.40.

EXAMPLE 16

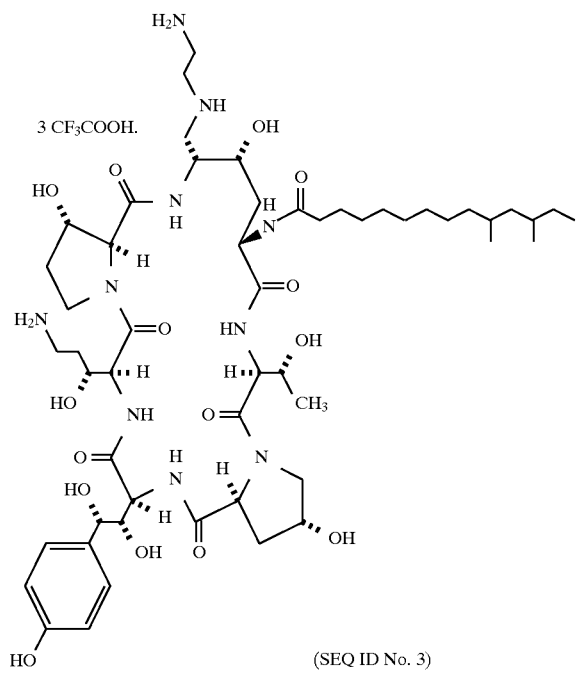

(SEQ ID No. 3)

A suspension of the bisamine ditrifluoroacetate from Example 15 (169 mg, 0.125 mmol) in anhydrous tetrahydrofuran (10 ml) is cooled to 0°–4° C. Neat $BH_3 \cdot S(CH_3)_2$ (107 mg, 1.41 mmol) is added slowly. The resulting reaction mixture is stirred at ca. 0° C. for a period of 4 h. The mixture is slowly quenched with 2N HCl (352 μl) and diluted with water. Preparative C18 HPLC of this solution eluting with $CH_3CN/H_2O$ (0.1% $CF_3COOH$) followed by lyophilization of the product-containing fractions provides the trisamine shown above as the tritrifluoroacetate salt: $C_{59}H_{93}F_9N_{10}O_{21}$, formula weight=1449.44.

EXAMPLE 17

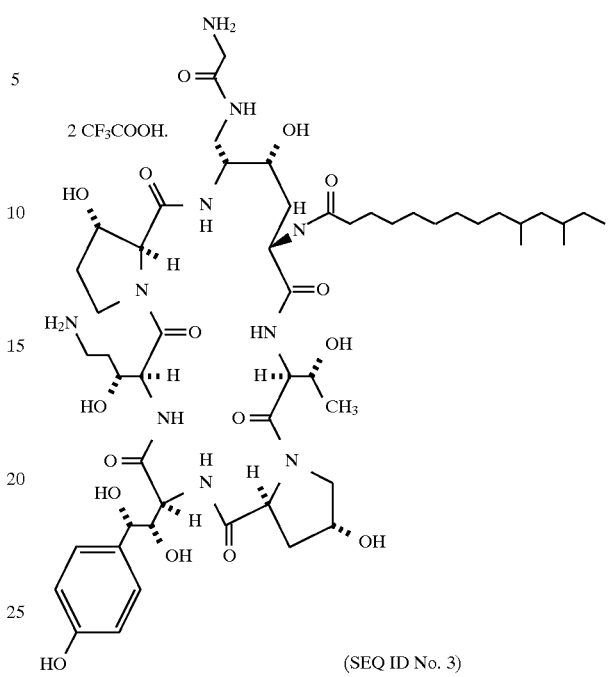

(SEQ ID No. 3)

Part A: Preparation of CBZ Protected Amine

To a stirred solution of the starting amine trifluoroacetate from Example 1 (92 mg, 0.087 mmol) and benzyl 4-nitrophenyl carbonate (26.1 mg, 0.095 mmol) in anhydrous N,N-dimethylformamide (3.5 ml) is added triethylamine (24.3 μl, 0.174 mmol). The reaction mixture is stirred until C18-HPLC analysis indicates complete consumption of starting material. The reaction mixture is diluted with water (3.5 ml) and the product is isolated by C18 solid-phase extraction eluting initially with $CH_3CN/H_2O$ and then $CH_3OH$. Concentration of the product-containing $CH_3OH$ fractions as determined by analytical HPLC gives crude CBZ intermediate: $C_{59}H_{87}N_9O_{17}$, formula weight=1194.4.

Part B: Reduction of Nitrile

In a manner similar to that described in Example 2, the nitrile from Part A is reduced and the amine product is isolated as the trifluoroacetate salt: $C_{61}H_{92}F_3N_9O_{19}$, formula weight=1312.46.

Part C: Preparation of the CBZ-Protected Glyamide

In a manner similar to that described in Example 11, Part A, the amine from Part B above is converted to a CBZ-protected glyamide derivative: $C_{69}H_{100}N_{10}O_{20}$, formula weight=1389.62.

Part D: Deprotection

In a manner similar to that described in Example 11, Part B, deprotection of the intermediate from Part C provides the glyamide derivative shown above as the diacetate salt. Purification by preparative C18-HPLC eluting with $CH_3CN/H_2O$ (0.1% $CF_3COOH$) provides the ditrifluoroacetate salt: $C_{57}H_{90}F_6N_{10}O_{20}$, formula weight=1349.4.

EXAMPLE 18

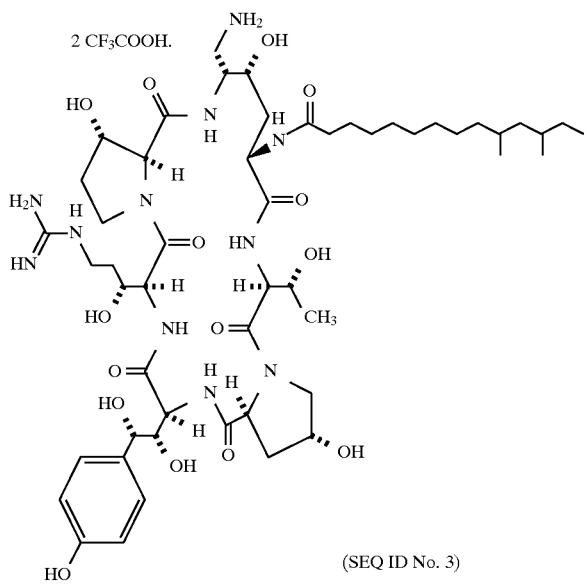

(SEQ ID No. 3)

Part A: Preparation of Guanidine

To a stirred solution of the starting amine trifluoroacetate from Example 1 (145 mg, 0.137 mmol) and 1M sodium bicarbonate (150 μl, 0.150 mmol) in absolute methanol (5 ml) is added aminoiminomethanesulfonic acid (30 mg, 0.242 mmol). After a period of 1.5 h, the solvent is removed in vacuo. Preparative reverse-phase HPLC (C18) of the residue, eluting with acetonitrile/water (0.1% trifluoroacetic acid), is followed by lyophilization of the product-containing fractions to give the guanidine trifluoroacetate salt: $C_{54}H_{84}F_3N_{11}O_{17}$, formula weight=1216.33.

Part B: Reduction of Nitrile

In a manner similar to that described in Example 2, the nitrile from Part A is reduced and the product shown above is isolated as the bistrifluoroacetate salt: $C_{56}H_{89}F_6N_{11}O_{19}$, formula weight=1334.39.

The following non-limiting examples illustrate representative compositions containing the compounds of the invention.

COMPOSITION EXAMPLE A 1000 compressed tablets each containing 500 mg of the compound of Example 4 are prepared from the following formulation:

| Compound | Grams |
|---|---|
| Compound of Example 4 | 500 |
| Starch | 750 |
| Dibasic calcium phosphate, hydrous | 5000 |
| Calcium stearate | 2.5 |

The finely powdered ingredients are mixed well and granulated with 10 percent starch paste. The granulation is dried and compressed into tablets.

EXAMPLE B 1000 hard gelatin capsules, each containing 500 mg of the compound are prepared from the following formulation:

| Compound | Grams |
|---|---|
| Compound of Example 4 | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE C

An aerosol composition may be prepared having the following formulation:

|  | Per Canister |
|---|---|
| Compound of Example 4 | 24 mg |
| Lecithin NF Liquid Concd. | 1.2 mg |
| Trichlorofluoromethane, NF | 4.026 g |
| Dichlorodifluoromethane, NF | 12.15 g |

EXAMPLE D 250 milliliters of an injectable solution may be prepared by conventional procedures having the following formulation:

Dextrose 12.5 g
Water 250 ml
Compound of Example 4 400 mg

The ingredients are blended and thereafter sterilized for use.

PREPARATION OF STARTING MATERIALS

Compounds where $R^I$ is dimethyltridecyl and $R_1$ is OH, $R_2$ is H, $R_3$ is $CH_2CONH_2$, $R_4$ is $CH_3$ and $R_6$ is OH may be produced by cultivating Zalerion arboricola ATCC 20868 in a nutrient medium containing mannitol as the primary source of carbon as described in U.S. Pat No. 5,021,341 issued Jun. 4, 1991.

Compounds in which $R_3$ is H and $R^I$ is 11-methyltridecyl may be produced by cultivating Aspergillus sydowi in nutrient medium as descirbed in J. Antibiotics XL (No. 3) p.28 (1987).

Compounds in which $R_3$ is $CH_3$ and $R^I$ is linoleyl may be produced by cultivating Aspergillus nidulans NRRL 11440 in nutrient medium as described in U.S. Pat No. 4,288,549 issued Sep. 8, 1981.

Compounds in which $R_3$ is $CH_2CN$ may be produced by the reaction of a compound having a carboxamide group in the corresponding position with excess cyanuric chloride in an aprotic solvent. Molecular sieves may be employed in this reaction. After completion of the reaction, the sieves, if employed, are removed, and the filtrate concentrated to obtain the nitrile compound as more fully described in U.S. Pat No. 5,348,940 issued Sep. 20, 1994.

Compounds in which $R_3$ is $CH_2CH_2NH_2$ may be produced by either a chemical or catalytic reduction of the nitrile. It is conveniently carried out employing large molar excess of sodium borohydride with cobaltous chloride as more fully described in copending application Ser. No. 936,558 filed Sep. 3, 1992.

Compounds in which $R_3$ is $CH_2CH_2NH_2$ may also be directly prepared from the carboxamide employing a large molar excess of diborane.

Compounds in which $R_5$ is OH or $OSO_3H$ are described in European Patent Applications 0 431 350 and 0 462 531 by Fujisawa Pharmaceutical Co., Ltd.

Starting materials in which R' is a different group from that of the natural product may be obtained by deacylating the lipophilic group of the natural product by subjecting the natural product in a nutrient medium to a deacylating enzyme until substantial deacylation occurs, said enzyme having first been obtained by cultivating a microorganism of the family Pseudomondaceae or Actinoplanaceae, as described in Experentia 34, 1670 (1978) or U.S. Pat No. 4,293,482, recovering the deacylated cyclopeptide, and thereafter acylating the deacylated cyclopepetide by mixing together with an appropriate active ester R'COX to obtain Compound A with the desired acyl group.

The active esters R'COX may be prepared by methods known to the skilled chemist as illustrated in the following examples. Although any active ester is appropriate, the compounds are illustrated with pentafluorophenyl esters.

Preparation of Alkoxy Terphenyl Side Chains

The terphenylcarboxylic acid esters may be prepared through the following sequence of reactions, illustrated with a specific example as follows:

A. Preparation of pentyloxy-substituted-terphenyl-carboxylic acid

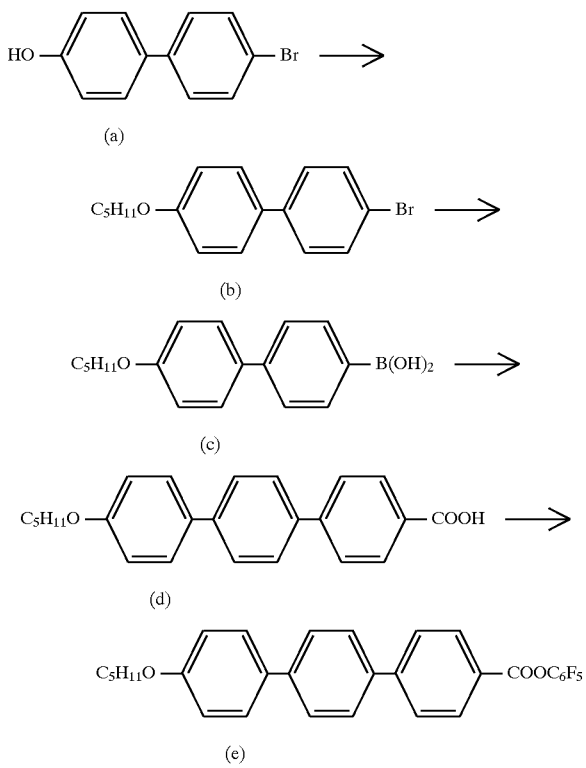

Part A: 4-(4-n-Pentyloxyphenyl)bromobenzene

To a stirred solution of 25.5 g of 4-(4-bromophenyl)phenol (Compound (a)) in 400 mL of dimethylsulfoxide was added 40.9 mL of 2.5N NaOH, followed by 12.7 mL of n-pentyl bromide, and the resulting mixture heated at 70° C. for 18 hours to obtain in the mixture, compound (b). The mixture was partitioned between 1000 mL of ethyl acetate and 500 mL water and from the organic phase after washing with water and brine, and drying was obtained 30.9 grams of Compound (b) as a white solid.

$^1$H NMR (400 MHz, DMSO-d$_6$) δ 0.93 (t, J=7.2 Hz, 3H), 1.41 (m, 4H), 1.79 (m, 2H), 3.97 (t, J=6.6 Hz, 2H), 6.94 (d, J=8.8 Hz, 2H), 7.39 (d, J=8.6 Hz, 2H), 7.45 (d, J=8.8 Hz, 2H), 7.51 (d, J=8.6 Hz, 2H).

Part B: 4-(4-n-Pentyloxyphenyl)phenylboronic acid

To a stirred suspension of 1.0 grams of Compound (b) in 20 mL anhydrous tetrahydrofuran at −78° C. under a nitrogen atmosphere was added 1.32 mL of 2.5M n-butyl lithium in hexanes. After 15 minutes 0.760 mL of tri-isopropyl borate was added and the stirring continued at −78° C. for 15 minutes and then at 25° C. for 40 minutes. The mixture was acidified and partitioned between ether and water to obtain the boronic acid compound (c) in the reaction mixture. The compound was recovered by washing with water and brine and drying to obtain 750 mg of 4-(4-n-pentyloxyphenyl)phenylboronic acid as white solid with the following $^1$H NMR.

$^1$H NMR (400 MHz, DMSO-d$_6$) δ 0.89 (t, J=7.2 Hz, 3H), 1.38 (m, 4H), 1.72 (m, 2H), 3.99 (t, J=6.5 Hz, 2H), 6.99 (d, J=8.8 Hz, 2H), 7.57 (d, J=8.2 Hz, 2H), 7.60 (d, J=8.8 Hz, 2H), 7.83 (d, J=8.2 Hz, 2H).

Part C: Pentafluorophenyl 4"-(n-pentyloxy)-[1,1':4',1"-terphenyl]-4-carboxylate

To a stirred mixture of 1.0 g of the boronic acid and 0.0874 mL of 4-iodobenzoic acid in 11 mL ethanol and 30 mL toluene was added 5.3 mL of a 2M aqueous solution of sodium carbonate followed by 204 mg tetrakis(triphenylphosphine)palladium and the reaction mixture heated under reflux (100° C.) for 18 hours. Thereafter, the mixture was cooled, acidified and partitioned between ethyl acetate and water. The organic phase was washed with water and brine and dried, then filtered through a bed of celite to obtain after removal of solvent and purification with flash silica gel chromatography to obtain 4"-(n-pentyloxy)-[1,1':4',1"-terphenyl]-4-carboxylic acid.

$^1$H NMR (400 MHz, DMSO-d$_6$) δ 0.89 (t, 3H), 1.37 (m, 4H), 1.72 (m, 2H), 3.98 (t, 2H), 7.01 (d, 2H).

To a mixture of 4"-(n-pentyloxy)-[1,1':4',1"-terphenyl]-4-carboxylic acid (10.5 mmol) and dicyclohexylcarbodiimide (10.5 mmol) in ethyl acetate at 0° C. is added pentafluorophenol (11.5 mmol). The mixture is stirred at 25° C. for a period of 18 h, producing a precipitate. The mixture is filtered. The filtrate is washed with water and brine and dried with magnesium sulfate. The solvent is removed in vacuo to obtain pentafluorophenyl 4"-(n-pentyloxy)-[1,1':4',1"-terphenyl]-4-carboxylate, C$_{30}$H$_{23}$F$_5$O$_3$, M.W.=526.5.

Preparation of Alkoxy Biphenyl Side Chains

The biphenylcarboxylic acid esters may be obtained through the following sequence of reactions illustrated as follows:

A. Preparation of Octyloxybiphenylcarboxylic acid

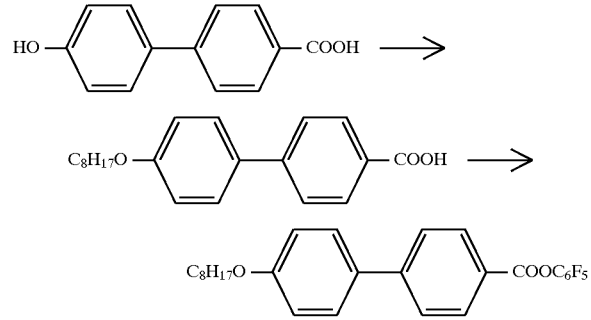

The acid is prepared as described in EP 462531 by Fujisawa Pharmaceutical Co., Ltd.

B. Preparation of pentafluorophenyl Ester

Pentafluorophenol (11.5 mmol) is added at 0° to a mixture of 10.5 mmol 4'-n-octyloxy[1,1'-biphenyl]-4-ylcarboxylic acid and 10.5 mmol of dicyclohexylcarbodiimide in ethyl acetate. The mixture is stirred at 25° C. for a period of 18 hours whereupon a precipitate is formed. The reaction mixture is filtered, the filtrate washed with water and brine and dried, the solvent removed in vacuo to obtain pentafluorophenyl 4'-n-octyloxy[1,1'-biphenyl]-4-ylcarboxylate, $C_{27}H_{25}F_5O_3$, M.W. 492.5.

Preparation of AminoethyloxyBiphenyl Side chains

Preparation of 4'-(2-[4-Cyclohexylmethylpiperidin-1-yl]ethoxy)-[1,1'-biphenyl]-4-ylcarboxylic acid, Pentafluorophenyl Ester

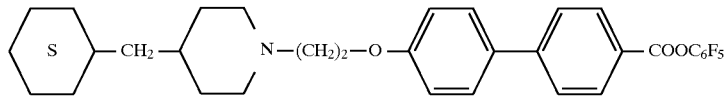

Part A: Preparation of 4-Cyclohexylmethylpiperidine

4-Benzylpiperidine is dissolved in glacial acetic acid containing $PtO_2$ (approximately 50 wt percent). A Paar hydrogenator is used and the reaction vessel is flushed with $H_2$ and pressurized to 3 atm. The mixture is shaken for sufficient time to give reduction of the aromatic ring to the fully saturated product which is determined by the uptake of 3 molar equivalents of $H_2$. The black solid is filtered and the acetic acid removed by evaporation under reduced pressure to obtain the product as an acetate salt.

Part B: Preparation of 1-(2-Hydroxyethyl)-4-cyclohexylmethylpiperidine

The product from Part A (1.0 eq) is dissolved in dichloromethane containing an equimolar amount of diisopropylethyl amine. Ethylene oxide (10 eq) is added and the mixture is stirred until starting material is consumed. The desired product is obtained by removal of the solvent in vacuo followed by purification by column chromatography.

Part C: Preparation of 4'-(2-[4-cyclohexylmethylpiperidine-1-yl]ethoxy)-[1,1'-biphenyl]-4-ylcarboxylic acid 4'-Hydroxy-[1,1'-biphenyl-4-ylcarboxylic acid methyl ester (1.0 eq) is dissolved in dichloromethane and triphenylphosphine (1.3 eq) and the hydroxyethyl compound (1.0 eq) from Part B is added. Next, diethyl azodicarboxylate (1.3 eq) is added and the mixture is stirred until starting material is consumed. The mixture is diluted with dichloromethane and washed with water. The organic layer is dried with $MgSO_4$ and filtered. The solvent is removed in vacuo and the residue is dissolved in ethanol. An excess of 3N sodium hydroxide is added and the mixture stirred for several hours. The reaction is neutralized with 2N HCl and is extracted with ethyl acetate. The ethyl acetate layer is dried with $MgSO_4$, filtered and the solvent vaporized under reduced pressure. The desired product is obtained in substantially pure form by column chromatography.

Part D: Preparation of the Pentafluorophenyl Ester

The carboxylic acid (1.0 eq) and dicyclohexylcarbodiimide (1.0 eq) are dissolved in ethyl acetate and the solution is cooled to 0° C. Pentafluorophenol (1.05 eq) is added, the ice bath then is removed and the reaction stirred at ambient temperature for 18–24 h. An equal volume of ether is added, the mixture is filtered and the solvent removed in vacuo. The product (MW=587.64) may be obtained in a sufficiently pure form to be utilized for nucleus acylation.

Preparation of 4'-(2-[4-Undecylpiperizin-1-yl]-ethoxy)[1,1'-biphenyl]-4-ylcarboxylic acid, Pentafluorophenyl Ester

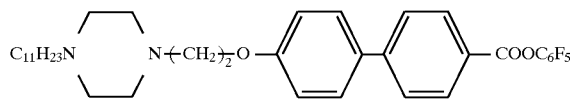

Part A: Preparation of 4-Undecylpiperazine

Excess piperazine (5 eq) and 1-bromoundecane (1.0 eq) are dissolved in dichloromethane and allowed to react overnight. The mixture is extracted with aqueous sodium bicarbonate and the organic layer dried with sodium sulfate. The mixture is filtered, the solvent removed in vacuo and the residue purified by column chromatography.

Part B: Preparation of 1-(2-Hydroxyethyl)-4-undecylpiperazine

The substituted piperazine above (1.0 eq) is dissolved in n-propanol and bromoethanol (1.0 eq) is added along with diisopropylethyl amine (1,1 eq). After several hours, the solvent is removed in vacuo and the residue dissolved in dichloromethane. The organic layer is washed with water and then aqueous sodium bicarbonate. The organic layer is dried with $MgSO_4$ and filtered. Removal of the solvent in vacuo is followed by purification by column chromatography.

Part C: Preparation of the Carboxylic Acid

The procedure is essentially the same as describe in Part C above except that the hydroxyethyl piperazine from above is substituted for the hydroxyethyl piperidine.

Part D: Preparation of the Pentafluorophenyl Ester

The procedure is identical to Part D from above except that piperazinyl-substituted-biphenyl carboxylic acid is used. The product (MW=646.75) may be obtained in a sufficiently pure form to be utilized "as is" in nucleus acylation.

Preparation of Pentafluorophenyl 6-Octyloxy-2-naphthoate

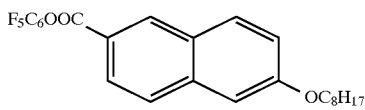

To a suspension of 6-octyloxy-2-naphthoic acid (3.15 g, 10.5 mmol) and dicyclohexylcarbodiimide in ethyl acetate (25 ml) at 0° C. was added pentafluorophenol (2.12 g, 11.5 mmol). The mixture was stirred at 25° C. for a period of 18 h. The precipitate was removed by filtration. The filtrate was washed with water (2×150 ml) and brine and dried with magnesium sulfate. Removal of the ethyl acetate in vacuo gave 5.4 g of pentafluorphenyl 6-octyloxy-2-naphthoate as a solid: $^1$H NMR (400 MHz, $CD_3OD$) δ 0.88 (t, 3, J=6.9 Hz), 4.10 (t, 2, J=6.6 Hz), 7.16 (d, 1), 7.21 (d, 1), 7.80 (d, 1), 7.87 (d,1), 8.08 (dd, 1), 8.69 (d, 1).

What is claimed is:

1. A compound having the formula

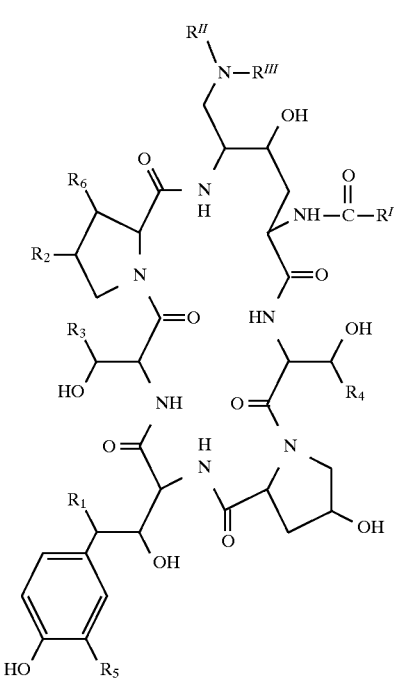

(I)
(SEQ ID NOS. 1–6)

wherein
 $R_1$ is OH;
 $R_2$ is H;
 $R_3$ is $CH_2CONH_2$, $CH_2CN$ or $CH_2CH_2NR^{II}R^{III}$;
 $R_4$ is $CH_3$;
 $R_5$ is H;
 $R_6$ is OH;
 $R^I$ is $C_9-C_{21}$ alkyl, $C_9-C_{21}$ alkenyl, $C_1-C_{10}$ alkoxyphenyl, $C_1-C_{10}$ alkoxynaphthyl, or

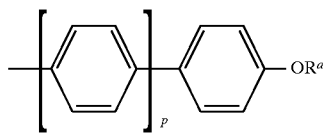

wherein
 $R^a$ is $C_1-C_{10}$ alkyl; or $(CH_2)_qNR^bR^c$ wherein $R^b$ and $R^c$ are independently H, $C_1-C_{10}$ alkyl or $R^b$ and $R^c$ taken together with
the nitrogen atom are

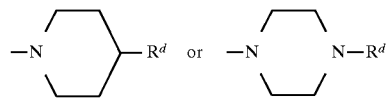

wherein
 $R^d$ is $C_1-C_{16}$ alkyl, cyclohexylmethyl, phenyl or benzyl;
 p is 1 or 2; and
 q is 2, 3 or 4;
 $R^{II}$ is H, $C_1-C_4$ alkyl, $(CH_2)_{2-4}OH$, $C=NH(R^{VII})$, $(CH_2)_{2-4}NR^VR^{VI}$, $(CH_2)_{2-4}N(R^{IV})_3{}^+X^-$, $(CH_2)_{2-4}NH(C=NH)R^{VII}$, $(CH_2)_{1-4}CH(NR^VR^{VI})(CH_2)_{1-4}NR^VR^{VI}$, $(CH_2)_{2-4}NR^V(CH_2)_{2-4}NR^VR^{VI}$, $CO(CH_2)_{1-4}NR^VR^{VI}$, $COCH(NR^VR^{VI})(CH_2)_{1-4}NR^VR^{VI}$;
 $R^{III}$ is H, $C_1-C_4$ alkyl, $(CH_2)_{2-4}NR^VR^{VI}$, $(CH_2)_{2-4}N(R^{IV})_3{}^+X^-$, $(CH_2)_{2-4}NH(C=NH)R^{VII}$, $(CH_2)_{1-4}CH(NR^VR^{VI})(CH_2)_{1-4}NR^VR^{VI}$, $(CH_2)_{2-4}NR^V(CH_2)_{2-4}NR^VR^{VI}$; or $R^{II}$ and $R^{III}$ taken together are $-(CH_2)_4-$, $-(CH_2)_5-$, $-(CH_2)_2O(CH_2)_2-$, or $-(CH_2)_2NH(CH_2)_2-$;
 $R^{IV}$ is $C_1-C_4$ alkyl;
 $R^V$ is H or $C_1-C_4$ alkyl;
 $R^{VI}$ is H or $C_1-C_4$ alkyl;
 $R^{VII}$ is H, $C_1-C_4$ alkyl or $NH_2$;
 X is Cl, Br or I; or
a pharmaceutically acceptable salt thereof.

2. A compound having the formula

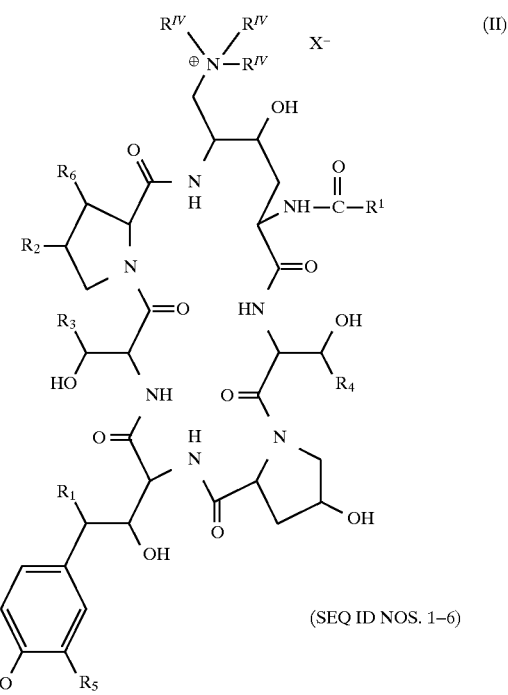

(II)

(SEQ ID NOS. 1–6)

wherein
 $R_1$ is OH;
 $R_2$ is H;
 $R_3$ is $CH_2CONH_2$, $CH_2CN$ or $CH_2CH_2NR^{II}R^{III}$;
 $R_4$ is $CH_3$;
 $R_5$ is H;
 $R_6$ is OH;
 $R^I$ is $C_9-C_{21}$ alkyl, $C_9-C_{21}$ alkenyl, $C_1-C_{10}$ alkoxyphenyl,
 $C_1-C_{10}$ alkoxynaphthyl, or

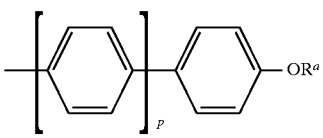

wherein
 $R^a$ is $C_1-C_{10}$ alkyl; or $(CH_2)_qNR^bR^c$ wherein $R^b$ and $R^c$ are independently H, $C_1-C_{10}$ alkyl or $R^b$ and $R^c$ taken together with
the nitrogen atom are

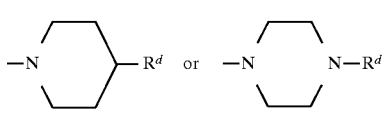

wherein $R^d$ is $C_1$–$C_{16}$ alkyl, cyclohexylmethyl, phenyl or benzyl;
p is 1 or 2;
q is 2, 3 or 4;
$R^{IV}$ is $C_1$–$C_4$ alkyl; and
X is Cl, Br or I.

3. A compound having the formula

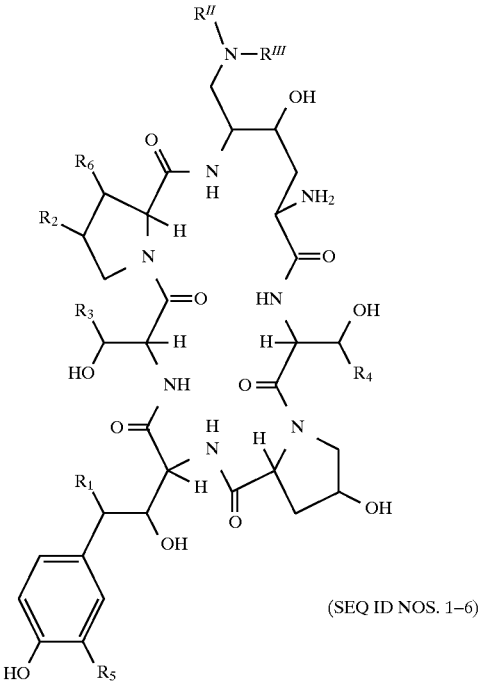

(III)

(SEQ ID NOS. 1–6)

wherein
$R_1$ is OH;
$R_2$ is H;
$R_3$ is $CH_2CONH_2$, $CH_2CN$ or $CH_2CH_2NR^{II}R^{III}$;
$R_4$ is $CH_3$;
$R_5$ is H;
$R_6$ is OH;
$R^{II}$ is H, $C_1$–$C_4$ alkyl, $(CH_2)_{2-4}OH$, $C=NH(R^{VII})$, $(CH_2)_{2-4}NR^VR^{VI}$, $(CH_2)_{2-4}N(R^{IV})_3^+X^-$, $(CH_2)_{2-4}NH(C=NH)R^{VII}$, $(CH_2)_{1-4}CH(NR^VR^{VI})(CH_2)_{1-4}NR^VR^{VI}$, $(CH_2)_{2-4}NR^V(CH_2)_{2-4}NR^VR^{VI}$, $CO(CH_2)_{1-4}NR^VR^{VI}$, $COCH(NR^VR^{VI})(CH_2)_{1-4}NR^VR^{VI}$;

$R^{III}$ is H, $C_1$–$C_4$ alkyl, $(CH_2)_{2-4}NR^VR^{VI}$, $(CH_2)_{2-4}N(R^{IV})_3^+X^-$, $(CH_2)_{2-4}NH(C=NH)R^{VII}$, $(CH_2)_{1-4}CH(NR^VR^{VI})(CH_2)_{1-4}NR^VR^{VI}$, $(CH_2)_{2-4}NR^V(CH_2)_{2-4}NR^VR^{VI}$; or $R^{II}$ and $R^{III}$ taken together are $-(CH_2)_4-$, $-(CH_2)_5-$, $-(CH_2)_2O(CH_2)_2-$, or $-(CH_2)_2NH(CH_2)_2-$;

$R^{IV}$ is $C_1$–$C_4$ alkyl;
$R^V$ is H or $C_1$–$C_4$ alkyl;
$R^{VI}$ is H or $C_1$–$C_4$ alkyl;
$R^{VII}$ is H, $C_1$–$C_4$ alkyl or $NH_2$;
X is Cl, Br or I; or a pharmaceutically acceptable salt thereof.

4. The compound as defined in claim 1 having the formula

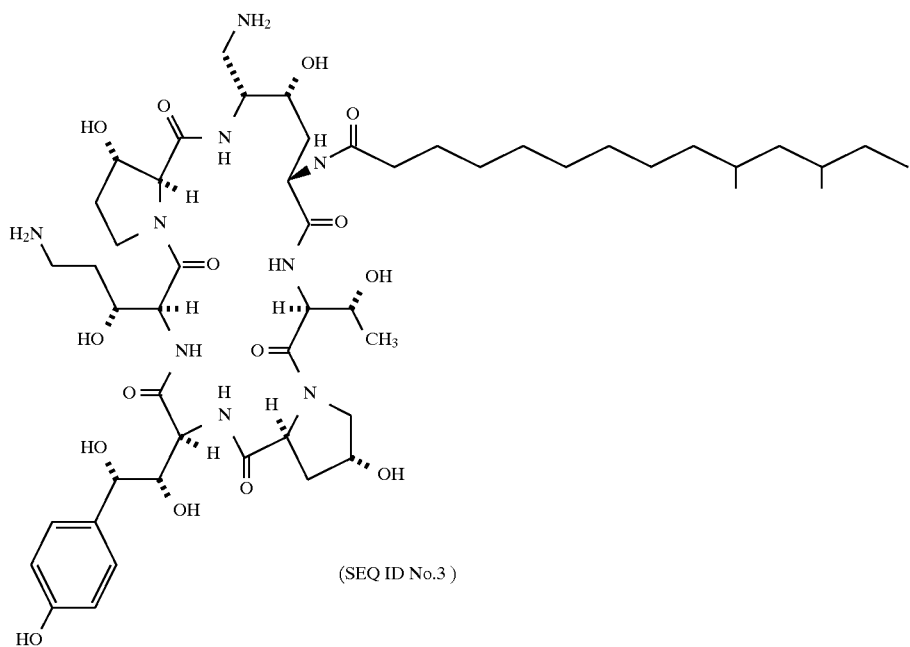
(SEQ ID No.3)
or a pharmaceutically acceptable salt thereof.
5. The compound as defined in claim 1 having the formula
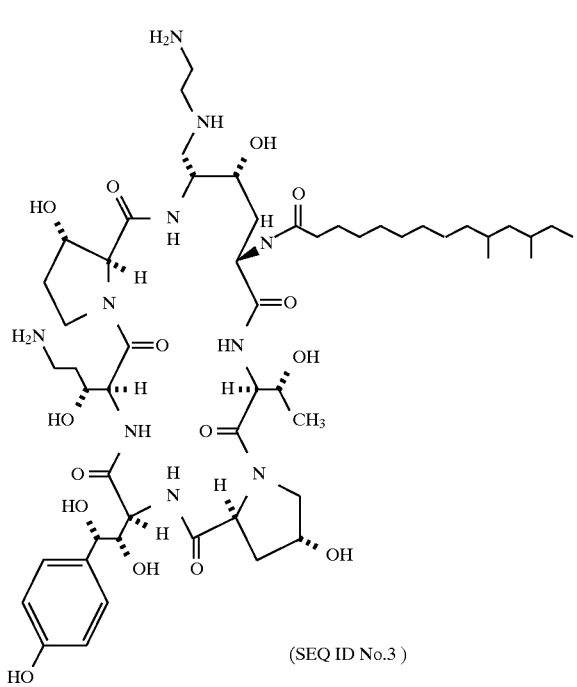
(SEQ ID No.3)
or a pharmaceutically acceptable salt thereof.
6. The compound as defined in claim 1 having the formula
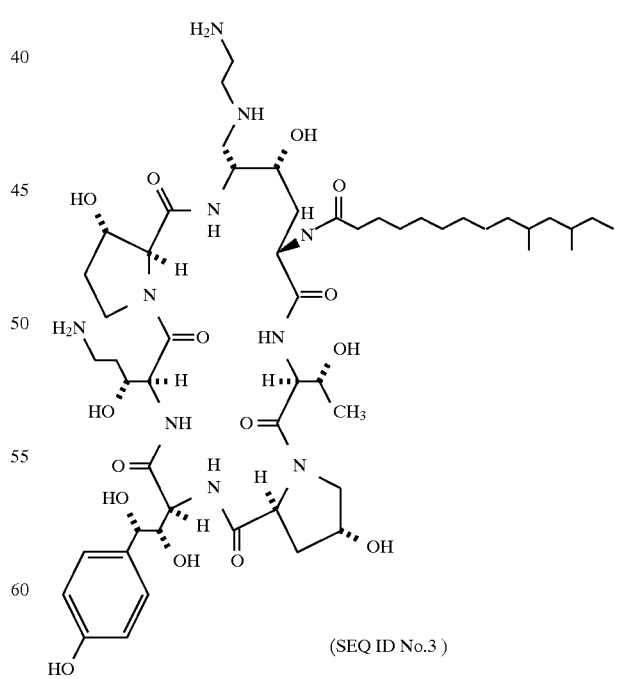
(SEQ ID No.3)
or a pharmaceutically acceptable salt thereof.

7. The compound as defined in claim 2 having the formula

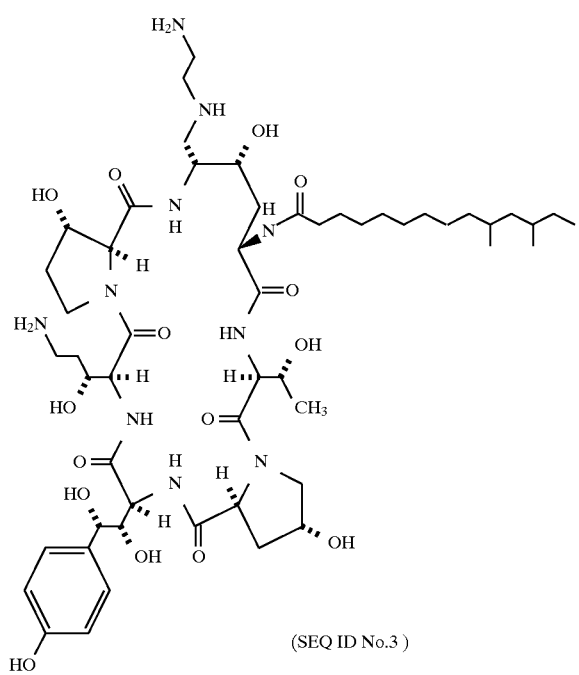

(SEQ ID No.3)

8. The compound as defined in claim 1 having the formula

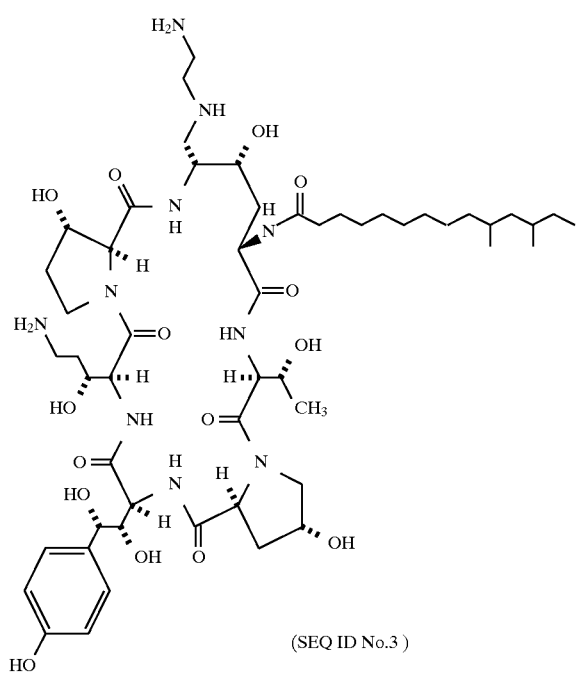

(SEQ ID No.3)

or a pharmaceutically acceptable salt thereof.

9. The compound as defined in claim 1 having the formula

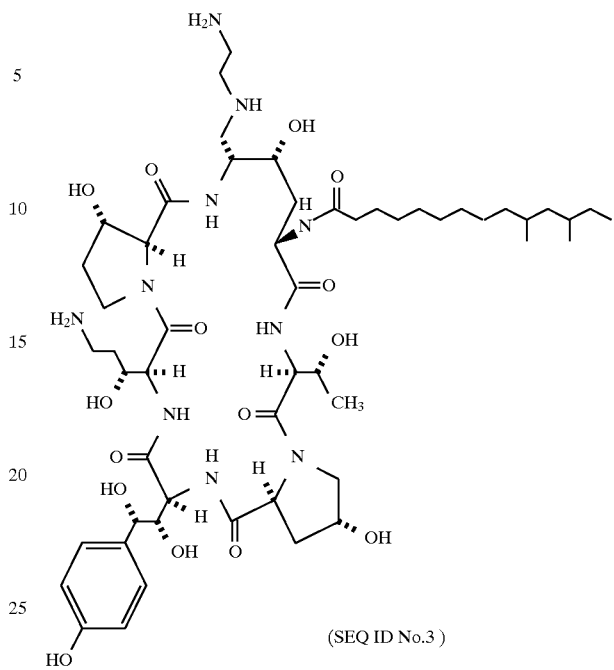

(SEQ ID No.3)

or a pharmaceutically acceptable salt thereof.

10. The compound as defined in claim 3 having the formula

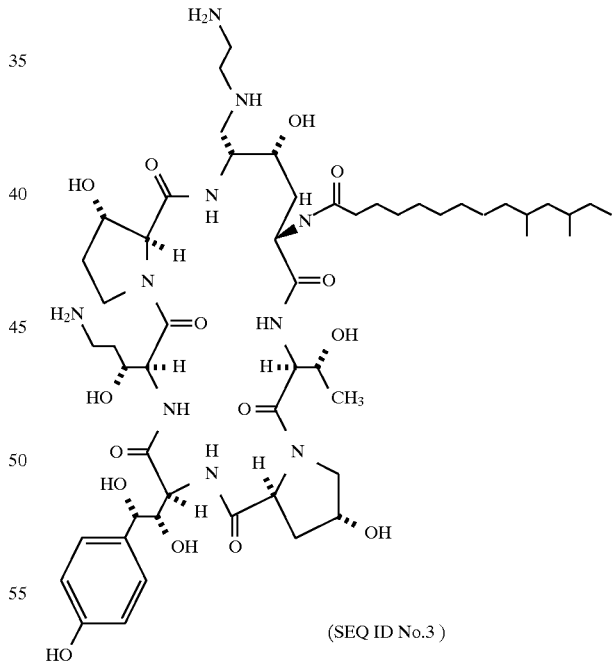

(SEQ ID No.3)

11. An antifungal composition comprising an effective amount of a compound as defined in claim 1 and a pharmaceutically acceptable carrier therefor.

12. A composition according to claim 11 in unit dosage form wherein the compound is present in an amount of 10 mg to 200 milligrams.

13. A method for treating fungal infections which comprises administering to a patient in need of said treatment a therapeutic amount of a compound as defined in claim 1.

14. A method for treating fungal infections caused by Candida sp. which comprises administering to a patient in need of said treatment a therapeutic amount of a compound as defined in claim 1.

15. A method for treating fungal infections caused by Aspergillus sp. which comprises administering to a patient in need of said treatment a therapeutic amount of a compound as defined in claim 1.

16. A method for treating a *Pneumocystis carinii* infection which comprises administering to a patient needing said treatment a therapeutic amount of a compound as defined in claim 1.

17. A method of preventing a *Pneumocystis carinii* infection in a patient which comprises administering to said patient a prophylactic amount of a compound as defined in claim 1.

* * * * *

UNITED STATES PATENT AND TRADEMARK OFFICE
CERTIFICATE OF CORRECTION

PATENT NO. : 5,854,213

DATED : December 29, 1998

INVENTOR(S) : Frances A. Bouffard

It is certified that error appears in the above-identified patent and that said Letters Patent is hereby corrected as shown below:

In Column 60, Line 30-55, should read:

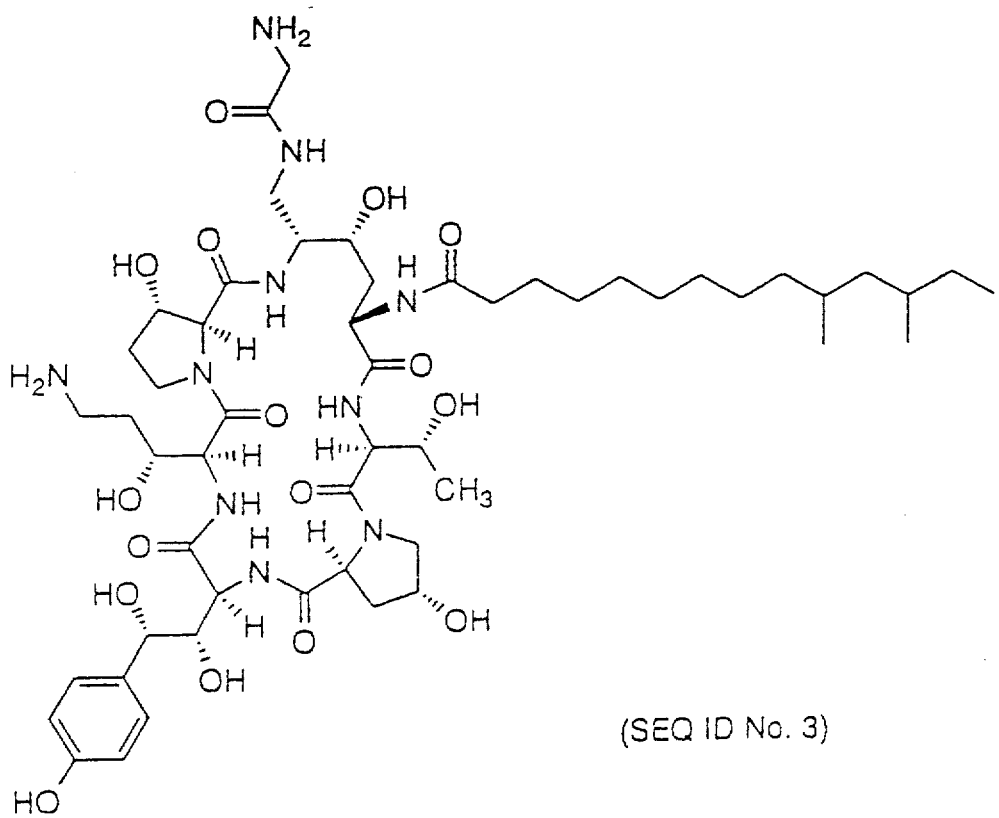

(SEQ ID No. 3)

UNITED STATES PATENT AND TRADEMARK OFFICE
CERTIFICATE OF CORRECTION

PATENT NO. : 5,854,213
DATED : December 29, 1998
INVENTOR(S) :
Frances A. Bouffard It is certified that error appears in the above-identified patent and that said Letters Patent is hereby corrected as shown below:

In Column 61, Line 5-30, should read:

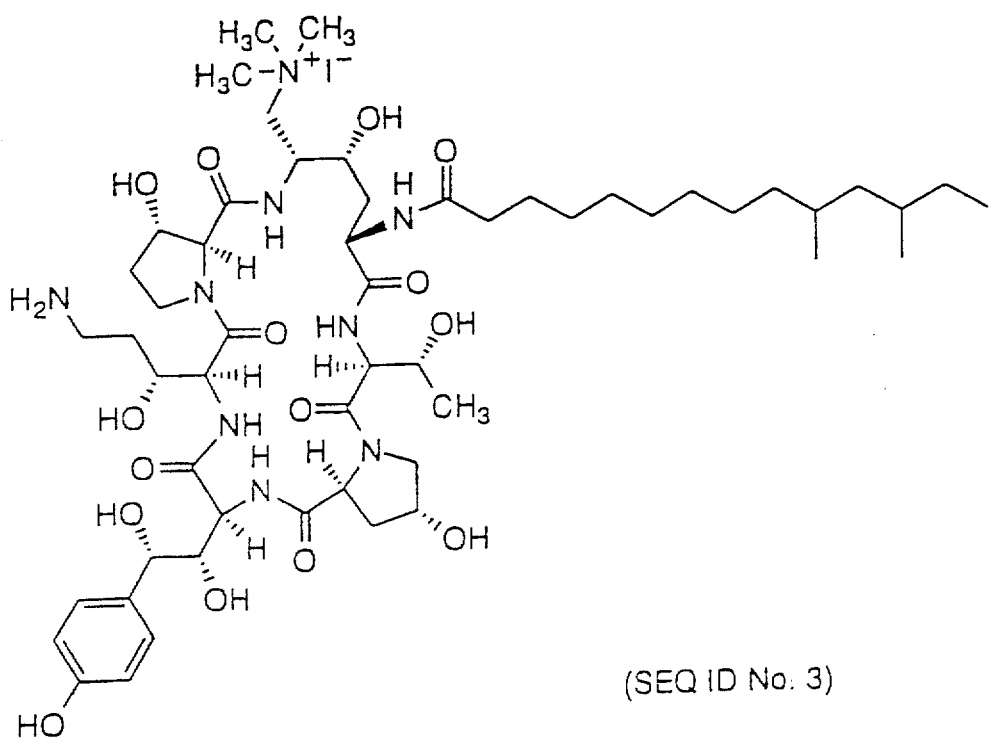

(SEQ ID No. 3)

UNITED STATES PATENT AND TRADEMARK OFFICE
CERTIFICATE OF CORRECTION

Page 3 of 5

PATENT NO. : 5,854,213
DATED : December 29, 1998
INVENTOR(S) :
Frances A. Bouffard It is certified that error appears in the above-identified patent and that said Letters Patent is hereby corrected as shown below:

In Column 61, Line 35-60, should read:

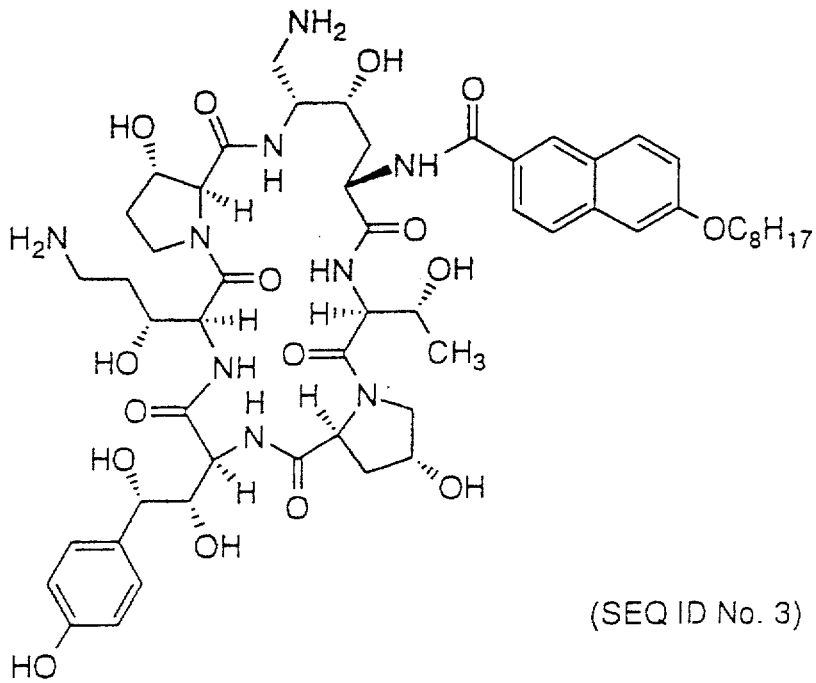

(SEQ ID No. 3)

UNITED STATES PATENT AND TRADEMARK OFFICE
CERTIFICATE OF CORRECTION

PATENT NO. : 5,854,213
DATED : December 29, 1998
INVENTOR(S) :
Frances A. Bouffard It is certified that error appears in the above-identified patent and that said Letters Patent is hereby corrected as shown below:

In Column 62, Line 5-25, should read:

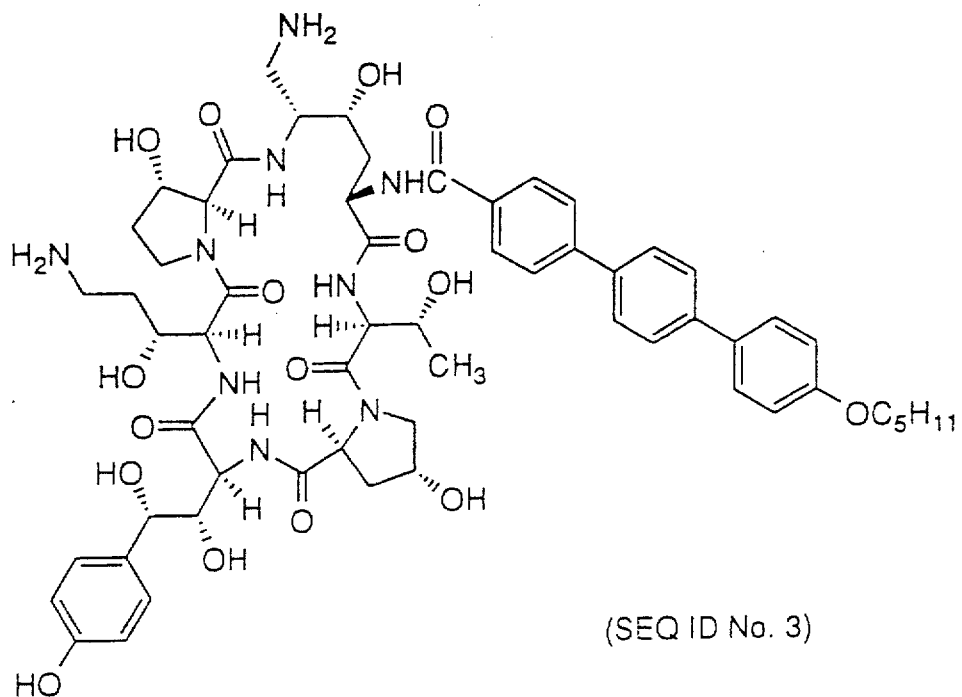

(SEQ ID No. 3)

UNITED STATES PATENT AND TRADEMARK OFFICE
CERTIFICATE OF CORRECTION

Page 5 of 5

PATENT NO. : 5,854,213
DATED : December 29, 1998
INVENTOR(S) :
Frances A. Bouffard It is certified that error appears in the above-identified patent and that said Letters Patent is hereby corrected as shown below:

In Column 62, Line 35-55, should read:

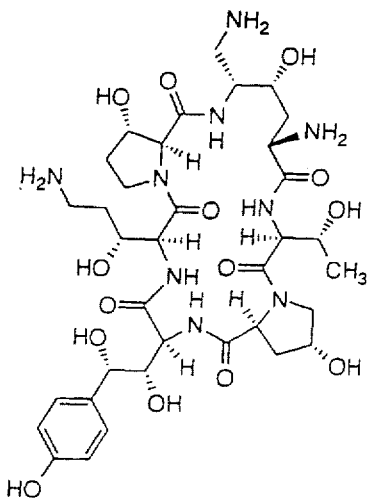

(SEQ ID No. 3)

Signed and Sealed this

Eleventh Day of May, 1999

Attest:

Q. TODD DICKINSON

Attesting Officer     Acting Commissioner of Patents and Trademarks